(12) United States Patent
Bublewitz et al.

(10) Patent No.: US 9,114,079 B2
(45) Date of Patent: Aug. 25, 2015

(54) POLYMERIZABLE DENTAL MATERIAL COMPRISING REACTIVE PASTE FORMERS, HARDENED DENTAL MATERIAL AND USE THEREOF

(75) Inventors: Alexander Bublewitz, Herborn (DE); Alexander Theis, Eschenburg (DE); Jens-Peter Reber, Meinerzhagen (DE)

(73) Assignee: Kettenbach GmbH & Co. KG, Frankfurt am Main (DE)

( * ) Notice: Subject to any disclaimer, the term of this patent is extended or adjusted under 35 U.S.C. 154(b) by 147 days.

(21) Appl. No.: 13/824,352

(22) PCT Filed: Sep. 23, 2011

(86) PCT No.: PCT/EP2011/066557
§ 371 (c)(1),
(2), (4) Date: May 13, 2013

(87) PCT Pub. No.: WO2012/052249
PCT Pub. Date: Apr. 26, 2012

(65) Prior Publication Data
US 2013/0225699 A1     Aug. 29, 2013

(30) Foreign Application Priority Data

Sep. 28, 2010 (DE) .......................... 10 2010 046 697

(51) Int. Cl.
*A61K 6/083* (2006.01)
*A61K 6/00* (2006.01)

(52) U.S. Cl.
CPC ............... *A61K 6/083* (2013.01); *A61K 6/0017* (2013.01); *A61K 6/0023* (2013.01); *A61K 6/0038* (2013.01)

(58) Field of Classification Search
CPC .............. A61K 6/083; C08F 2/44; C08F 4/40
USPC ........ 514/772.4; 525/201; 523/115, 109, 113, 523/120; 526/217, 220, 227
See application file for complete search history.

(56) References Cited

U.S. PATENT DOCUMENTS

| | | | |
|---|---|---|---|
| 3,347,854 A * | 10/1967 | Lenhard et al. | ................. 540/66 |
| 3,347,954 A | 10/1967 | Hellmut et al. | |
| 6,852,775 B1 * | 2/2005 | Soglowek et al. | ............ 523/109 |
| 2009/0192239 A1 | 7/2009 | Hecht et al. | |

FOREIGN PATENT DOCUMENTS

| | | |
|---|---|---|
| DE | 1495520 | 4/1969 |
| EP | 1194110 B1 | 4/2002 |
| EP | 2198824 A1 | 6/2010 |

OTHER PUBLICATIONS

Form PCT/IB/388, Notification of Transmittal of Translation of the International Preliminary Report on Patentability.

* cited by examiner

*Primary Examiner* — Robert Harlan
(74) *Attorney, Agent, or Firm* — McDonnell Boehnen Hulbert & Berghoff LLP

(57) ABSTRACT

A polymerizable dental material containing reactive paste-forming agent hardened dental material and the use thereof.

37 Claims, No Drawings ature, must therefore be stored separate from the co-initiator while storing the dental materials. Consequently, most of the time, multicomponent systems are used for which the components are only brought in contact with each other directly prior to processing the dental material, and are carefully mixed with each other.

POLYMERIZABLE DENTAL MATERIAL COMPRISING REACTIVE PASTE FORMERS, HARDENED DENTAL MATERIAL AND USE THEREOF

CROSS REFERENCE TO RELATED APPLICATIONS

The present application is a 35 U.S.C. 371 National Application of PCT/EP2011/066557 filed Sep. 23, 2011, which claims priority to German Patent Application No. 102010046697.2, filed Sep. 28, 2010, the entire contents of which are incorporated entirely herein by reference.

The present invention relates to a polymerizable dental material in the form of a paste-like multicomponent formulation containing at least one monomeric, oligomeric and/or polymeric reactive paste-forming agent, mono, bio or oligo to poly-functional acrylic acid esters and/or methacrylic acid esters (hereinafter jointly "(meth)acrylic acid esters") and barbituric acid derivatives and/oder malonyl sulfamides. The invention further relates to a polymerized dental material and to the use of the polymerizable and the polymerized dental material, for example, as crown or bridge material.

These types of materials are used, for example, for making multipart bridges, crowns, inlays, onlays or temporary pin restoration pieces subsequent to endodontic treatment.

Prosthetic dentistry knows a direct and an indirect method for producing temporary restoration pieces. The direct method is understood to be the production of the temporary pieces directly by the dentist subsequent to preparation. Indirect production consists of manufacturing a model in the laboratory.

In this way, for example, temporary crowns and bridge materials are produced in dentistry to cover the dentin wound after preparations have been made, or also for the temporary care of implant structures. When caring for natural tooth stumps, they are used to protect the dental pulp from thermal, chemical and bacterial influences. Additional tasks lie in maintaining the chewing function, fixing the occlusal or sagittal jaw relationship and preventing ingrowing of the adjacent gingiva on the tooth stump.

Prior to the preparation of the affected tooth, an impression is taken of the corresponding jaw section that identifies the original situation and the shape of the tooth that is to be prepared. After the preparation, the impression of the ground down tooth in the impression is filled with the temporary crown and bridge material. The impression prepared in this way is aligned with the jaw. When the temporary crown and bridge material has reached a rubbery-elastic state, the impression with the shaped, raw temporary arrangement can be removed and processed after it has hardened completely, and can be ground down adapted to the tooth stump and the occlusion (chewing surface). The temporary piece is inserted with special, temporary fastening cements.

Generic, polymerizable dental materials are known in prior art in principle. They contain polymerizable monomers that are polymerized by radicals that have been formed. As a rule, these radicals are formed by the reaction of a suitable initiator together with a co-initiator, whereby the radical formation starts immediately after they are brought together. The initiator, which has sufficient storage stability by itself at room temperature, must therefore be stored separate from the co-initiator while storing the dental materials. Consequently, most of the time, multicomponent systems are used for which the components are only brought in contact with each other directly prior to processing the dental material, and are carefully mixed with each other.

An initiator system known in prior art for generic dental material most often has an aromatic amine in combination with an organic peroxide, as is described, for example, in DE 975 072, whereby the redox reaction between amine and peroxide supplies the radicals. However, such amine-based initiator systems have significant disadvantages, in particular, toxic and/or allergenic effects of the components and their successor products, and generally, had color stability. These and additional disadvantages are described in detail in EP 1 872 767 A1.

Furthermore, in this publication, while appreciating prior art, as alternatives to the known initiator systems, CH-acidic compounds, in particular barbituric acid derivatives in combination with transition metal ions and chloride ions are cited. This alternative initiator system has a more favorable temperature progression during polymerization and the polymerizates that are obtained have significantly better color stability.

In initiator systems based on barbituric acid or its derivatives, the barbituric acid (derivatives) must be stored separate from the polymerizable monomers. This is because CH-acidic compounds such as the derivatives of barbituric acid form hydroperoxides by autoxidation with atmospheric oxygen already without the help of Cu(II) and chloride ions. These hydroperoxides break down by forming radicals, which initiate the polymerization of the reactive monomers so that spontaneous polymerization occurs within a short time. This spontaneous polymerization process CaO be suppressed or delayed for a short time (in the range of a few hours) by the addition of stabilizers, but not over a longer period of time as it is desired for systems with storage stability.

Relatively simple dental formulations with redox initiator systems, which contain barbituric acid (derivatives) as initiator components are known from DE 101 24 029 A1 and DE 38 06 740 C1 Powder/fluid systems are described there in which barbituric acid (derivatives) are stirred into the fluid monomer mixture in powdered form.

But because this is done by manual mixing, these systems are comparably difficult to dose and it is very difficult, if not impossible, to avoid air bubbles in the finished crown or bridge.

According to prior art, these types of problems are avoided by using so-called paste/paste systems. Thereby, the barbituric acid (derivatives) are dispersed in a paste consisting of inert plasticizers and fillers. In this process it is required that the component containing the initiator exclusively contains compounds that do not prematurely polymerize with CH-acidic compounds, i.e. the initiator components essentially contains non-polymerized compounds that do not have any double bonds.

EP 1 194 110 B1 discloses generic, polymerizable dental masses that contain at least one bi or higher functional ethylenically unsaturated monomer, at least one mono-functional ethylenically unsaturated monomer, one catalyst, a redox initiator system that can trigger the radical polymerization, fillers, thixotropic adjuvants, retarders and other adjuvants and a customary plasticizer, whereby the redox initiator system includes a barbituric acid derivative and/or a malonyl sulfamide and an organic peroxide selected from the group of single or multifunctional carboxylic acid peroxyesters.

Even the polymerized dental mass of EP 1 194 110 B1 has a certain proportion of unreacted components that are not integrated into the polymerized dental mass. These are the plasticizers customarily used in dental work. With respect to a polymerization, these are inert, i.e. they do not contain any radical polymerizable double bonds and are therefore not included in the polymerization. This is the reason why the mechanical properties of the polymerizates obtained in this way are in need of improvement. Beyond that, this type of unreacted components can be dissolved in the aggressive environment of the mouth and cause reactions that are harmful to health.

The invention described in EP 1 872 767 A1 was based on the objective of creating an initiator system for polymerizable dental materials that avoid the disadvantages known in prior art and which are beyond that, also usable in materials dosed 1:1 such as filling and veneering resins.

According to EP 1 872 767 A1, in contrast to the starter systems based on CH-acidic compounds in prior art, a precursor of the active starter molecule was used, namely, a salt of the CH-acidic compound. The CH-acidic compound is released only after the addition of an acid, the acidity of which is larger than the CH-acidic compound that is present as salt, and can subsequently function as starter molecule for the polymerization process of the monomers. According to EP 1 872 767 A1 it was identified that in contrast to the CH-acidic compounds in prior art, salts of the CH-acidic compound are stable for storage, even for longer periods of time. As a result, the initiator activity for the polymer reaction of the polymerizable monomers is ensured even when the components of the polymerizable dental material are stored for longer periods of time. According to this publication, pastes used to mix the polymerizable dental material, and in particular, pastes containing the salt of the CH-acidic compound, particularly preferred, are said to be color and/or storage stable for more than 24 months. The problem inherent in these types of formulations is that the release of the catalytically active free acid of the CH-acidic compound progresses very slowly and as a result, the hardening reactions last comparably long.

From EP 1 881 010 A1 and also EP 2 239 275 A1, polymerizable compounds are known that contain salts of barbituric acid derivatives and polymerizable monomers without acidic functionality in an initiator component, or in which a redox initiator system containing a salt of a barbituric acid derivative, an acidic component or a precursor of such and a copper compound are made available. Various formulations are described, among them paste/paste combinations. As mixtures of barbituric acid or barbituric acid derivatives with polymerizable ethylenically unsaturated compounds are not stable for storage, a salt of barbituric acid or a salt of a barbituric acid derivative is used in this case. Here as well, the initiation of the hardening reaction is caused by a combination of the salt of the barbituric acid or the barbituric acid derivative with the acidic compound, as a result of which the catalytic, active free acid of the CH-acidic compound is only released comparatively slowly.

A polymerizable dental material is known from EP 2 198 824 A1. It is formulated in at least two components A and B, whereby component A contains a special peroxide in addition to a radically polymerizable monomer without an acid group, and component B contains a radically polymerizable monomer without an acid group and a salt of a CH-acidic compound, which can trigger a radical polymerization as CH-acidic compound. Even in this polymerizable dental material, a precursor of the active CH-acidic starter molecule is used, namely, a salt of this CH-acidic compound. The combination of the salt of a CH-acidic compound with a selected ethylenically unsaturated monomer in component B affords sufficiently long storage stability. The salt of the CH-acidic compound, for example, a salt of barbituric acid or a salt of a barbituric acid derivative is activated only after the combination with the peroxide from component A and then causes a polymerization of the monomers present.

This composition of materials can easily be polymerized at room temperature in the absence of an acid. The material hardens well and has good mechanical properties.

In WO 2011/083020 A2, which has an older priority and in DE 10 2009 058 638 A1, which is parallel to it, multicomponent systems are described for producing a dental material. One component contains at least one radical polymerizable resin and at least one polymerization catalyst and the second component contains an inert matrix that is liquid or paste-like at room temperature and/or at least one radically polymerizable resin, and at least one CH-acidic compound, or a salt thereof as polymerization initiator. In one or both components, this system contains a perester, a peracetal or a perketal. In the event that in the second component (i.e. in the component containing the polymerization initiator) a radically polymerizable resin is provided, this publication requires that the polymerization initiator must be a salt of a CH-acidic compound. Even in this polymerizable dental material, only the combination of the salt of a CH-acidic compound with a radically polymerizable resin in the second component ensures sufficiently long storage stability. The salt of the CH-acidic compound, for example, a salt of barbituric acid or a salt of a barbituric acid derivative is activated only after combining both components, and then initiates a polymerization of the monomers present.

This makes it clear that initiator systems based on barbituric acid derivatives or malonyl sulfamides and ionogenically bound halogen and a heavy metal compound are in need of improvement with respect to their reaction kinetics and the mechanical properties after the polymerization.

It is assumed that this problem is significantly influenced by the presence of inert, non-reactive paste-forming agents.

For use in dentistry, materials having a particularly high degree of resistance are desirable. For example, dental masses for the production of crowns and bridges must be very break-resistant and also sufficiently stabilize the relation to the tooth stumps.

It is the objective of the present invention to provide a polymerizable paste-like two-component dental material by means of which the disadvantages known in prior art are avoided and simultaneously, excellent storage stability and reproducible and sufficiently short hardening times are ensured under mouth conditions. In particular, these types of dental materials can be processed into polymerizates with excellent mechanical properties.

In the polymerizable dental material according to the invention, this problem is solved thereby, that in the form of a multicomponent formulation, in particular, a two-component formulation consisting of components A and B is made available, wherein the individual components are present in the form of paste and contain selected ingredients. Thus, among other things, in component A, a reactive paste-forming agent a) with maleic acid and/or fumaric acid and/or itaconic acid units and/or a reactive paste-forming agent b) with terminal and/or lateral allyl and/or methallyl groups are used.

As the basis of the present invention it was identified that one of the causes of the disadvantages of prior art is due to the inert, i.e. non-reactive paste-forming agents used that do not contain any unsaturated carbon-carbon bonds.

Surprisingly, it was found that selected reactive paste-forming agents containing alkenyl groups can be formulated at room temperature and at a stress temperature of 40° C. or 60° C. and are stable for storage with barbituric acid derivatives and/or with malonyl sulfonamides as initiator paste A, without triggering a premature polymerization of the selected alkenyl groups. Beyond that, it was surprisingly found that barbituric acid derivatives and/or malonyl sulfonamide contained in storage-stable catalyst paste A and reactive paste-forming agents containing alkenyl groups copolymerize in radical polymerization after mixing with the compounds contained in base paste B of polymerizable (meth)acrylate groups under a mouth temperature (~35° C.) and that thereby, the reactive paste-forming agents containing alkenyl groups and the compounds containing (meth)acrylate groups are integrated into the network that is being created. Thereby, in contrast to the formulations in prior art that contain non-reactive paste-forming agents, significantly better mechanical final properties are achieved in the end product after the polymerization. This is documented, for example, by higher bending strengths and E-modulus in the three-point bending test.

Apparently, selected compounds containing alkenyl groups cannot be polymerized by the CH-acidic barbituric acid derivatives and/or malonyl sulfamides during storage in the absence of the co-initiators (metal ions such as, for example, Cu ions and halide ions), as is the case for (meth) acrylates and vinyl ethers (compare, for example, DE 10 017 188 B4). On the other hand, these selected alkenyl compounds in the polymerization of the (meth)acrylate under mouth temperature are also being polymerized as co-monomers and lead to better mechanical properties than those of masses known in prior art. It is a further advantage that by including the selected alkenyl groups contained in the reactive paste-forming agents, compared with the non-reactive paste-forming agents without alkenyl used in prior art, e.g. 2,2 bis-4-(2-hydroxyethoxyphenyl)propane bisacetate (DE 10 017 188), polyethylene glycol (EP 0 563 749 A1), phthalate, polyester, the proportion of the dissolvable compounds becomes smaller, and as a result, a higher degree of biocompatibility can be expected.

Therefore, the present invention concerns a polymerizable dental material containing at least one paste-like component A and at least one paste-like component B, whereby component A contains at least one initiator of the radical polymerization c) selected from the group of barbituric acid derivatives and/or malonyl sulfamides, and whereby component B contains an organic compound d) including at least one acrylic acid ester and/or methacrylic acid ester residues, at least one metal compound e) and at least one halide and/or pseudo-halide compound f), and whereby the polymerizable dental material is characterized in that component A as reactive paste-forming agent has at least one organic compound a) derived from maleic acid and/or fumaric acid and/or from itaconic acid, that has no additional ethylenically unsaturated groups in addition to those derived from maleic acid and/or fumaric acid and/or itaconic acid, and/or at least one compound b) including at least one allyl and/or methallyl residue and perhaps units derived from maleic acid and/or fumaric acid and/or itaconic acid which do not contain any further ethylenically unsaturated groups in addition to the aforementioned ethylenically unsaturated groups.

Ingredient a) can be any organic compound derived from maleic acid and/or fumaric acid and/or itaconic acid. In addition to the aforementioned ethylenically unsaturated residues, these compounds have no further ethylenically unsaturated residues such as, for example, vinyl ether groups and/or (meth)acrylate groups.

The organic compounds derived from maleic acid and/or fumaric acid and/or itaconic acid can be monomeric, oligomeric or polymeric compounds. Examples of monomeric compounds are maleic acid, fumaric acid and/or itaconic acid and their derivatives such as, for example, their mono or diesters, mono or diamides or anhydrides. Examples of such derivatives are mono or dialkylesters and fumaric acid, maleic acid or itaconic acid anhydrides.

Preferably, polymerizable denial materials containing at least one paste-like component A and at least one paste-like component B with the aforementioned ingredients a) to f) in the aforementioned distribution to the components A and B, whereby component A as reactive paste-forming agent contains at least one organic compound a) derived from maleic acid and/or fumaric acid, which has no further ethylenically unsaturated groups in addition to the groups derived from maleic acid and/or fumaric acid, and/or at least one compound b) including at least one allyl and/or methallyl residue and perhaps units derived from maleic acid and/or fumaric acid that have no further ethylenically unsaturated groups in addition to the aforementioned ethylenically unsaturated groups.

Preferably, these compounds contain groups of maleic acid and/or fumaric acid amides, and most particularly preferred, of maleic acid and/or fumaric acid diesters. Particularly preferred, these are organic compounds represented by the Formulas Ia, Ib, IIa, IIb, and in particular, Formulas IIc or IId

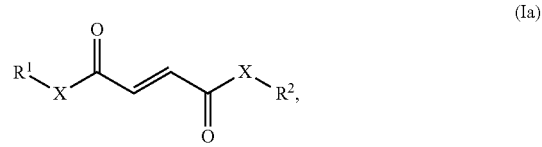

(Ia)

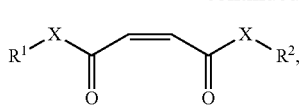
(Ib)

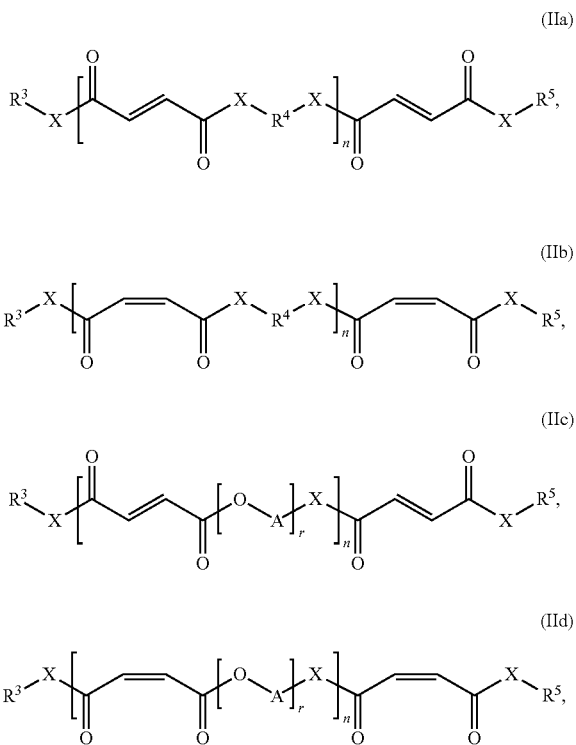

(IIa)

(IIb)

(IIc)

(IId)

in which X is oxygen or a group is represented by —NR$^6$—,
R$^1$, R$^2$, R$^3$ and R$^5$ mean, independent of each, other hydrogen, alkyl, cycloalkyl, aryl, aralkyl or heterocyclyl, which may have one or several substituents,
R$^4$ means alkylene, alkylene glycol ether, cycloalkylene, arylen, aralkylen or heterocyclylene, which may have one or several substituents,
A=CH$_2$—CH$_2$, CH$_2$—CH(CH$_3$) or CH$_2$—CH$_2$—CH$_2$—CH$_2$,
R$^6$ is hydrogen, alkyl, cycloalkyl, aryl, aralkyl or heterocyclyl,
n is a whole number from 1 to 50 and
r a whole number from 1 to 100.

One or more of the aforementioned residues R$^1$ to R$^5$ can be substituted, if appropriate. Examples of substituents are described below.

In one embodiment, one or more of the aforementioned residues R$^1$ to R$^5$ has/have substituents with acidic function such as, for example, phosphoric acid groups, phosphonic acid groups sulfonic acid groups and/or carboxylic acid groups and their anhydrides. Dental masses having such compounds containing free acid groups are particularly suited for use as self-etching dental cements.

In a further embodiment, one or more of the aforementioned residues R$^1$ to R$^5$ also have hydroxyl groups as substituents in addition to the substituents with acidic function and/or mixtures of acid-functionalized and hydroxy-functionalized compounds as represented by the Formulas Ia, Ib, IIa, IIb, IIc and/or IId are used. Such reactive paste-forming agents a) preferably used according to the invention can have, for example, unconverted free carboxyl and/or hydroxyl end groups and/or such groups in which free acid functions and/or hydroxy functions have been modified by functionalization with acidic compounds, for example by reaction with phosphorous pentoxide.

In practice, the compounds represented by the Formulas IIa, IIb, IIc and IId will frequently be present as statistic mixtures of maleic and fumaric acid esters or amides as well as polyesters or polyamides with various chain lengths. Beyond that, even mixed forms of the compounds represented by the Formulas IIa and IIb or IIc and IId can occur in which one molecule has units of the fumaric acid as well as the maleic acid.

Preferred components a) are mixtures of two or more of the Formulas Ia, Ib, IIa, IIb, IIc and IId and/or mixtures of compounds in which the index n and the index r take on different values within the scope of the given definition.

Examples of particularly preferred reactive paste-forming agents a) used according to the invention are:

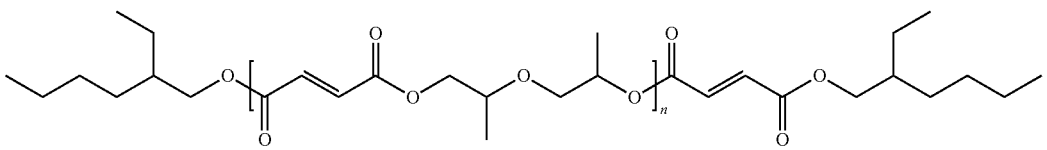

where n=0, 1, 2, 3, . . . 30

Alternative to the compounds shown above with di-propylene glycol units [—O—CH$_2$—CH(CH$_3$)—]$_2$ preferably also compounds having propylene glycol units [—O—CH$_2$—CH(CH$_3$)—]$_r$ or having ethylene glycol units [—O—CH$_2$—CH$_2$—]$_r$ or having butylene glycol such as tetramethylene glycol units, [—O—CH$_2$—CH$_2$—CH$_2$—CH$_2$—]$_r$ or having cyclopentylene units [—O—C$_5$H$_8$—]$_r$ or having cyclohexylene units [—O—C$_6$H$_{10}$—]$_r$ or having phenylene units [—O—C$_6$H$_4$—]$_r$ or having naphthylene units [—O—C$_{10}$H$_6$—]$_r$ or having benzylene units [—O—CH$_2$—C$_6$H$_4$—]$_r$ can be used. The index r can thereby be any whole number from 1 to 100.

Alternative to the compounds illustrated above that have 2-ethylhexanol units at the end of the chain, other univalent alcohols can also be used as end group such as, for example, benzyl alcohol or ethanol.

Further examples of a most particularly preferred use of reactive paste-forming agents a) with acid function are:

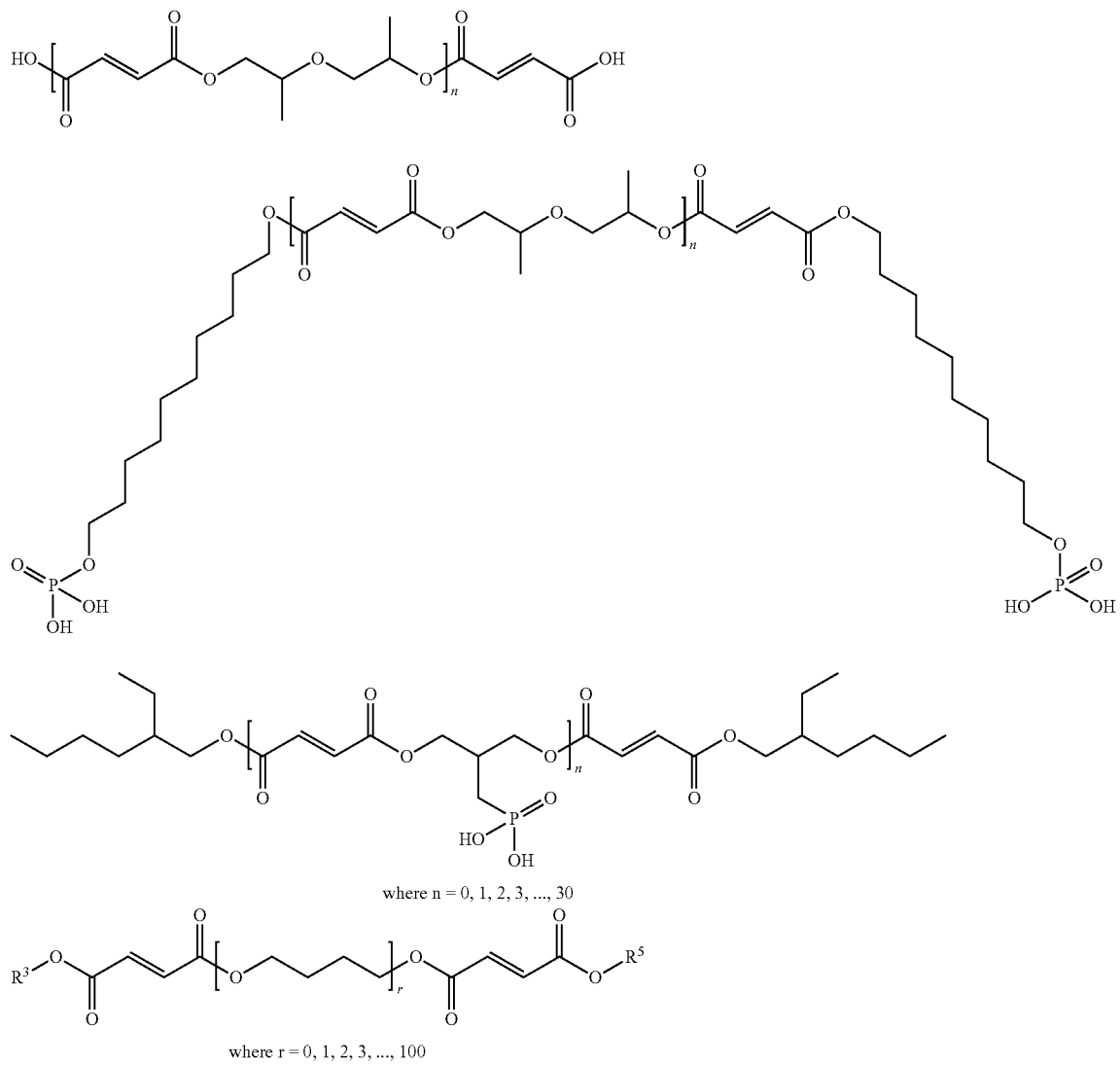

where n = 0, 1, 2, 3, ..., 30 where r = 0, 1, 2, 3, ..., 100

Whereby $R^3$ and $R^5$, independent of each other, mean hydrogen, alkyl, cycloalkyl, aryl, aralkyl or heterocyclyl, which perhaps have one or more substituents provided that at least one of the residues $R^3$ or $R^5$ mean hydrogen.

Ingredient b) can be any compound with at least one allyl and/or methallyl residue, which can perhaps still have units derived from fumaric acid and/or from maleic acid. Thereby, in addition to organic compounds, inorganic compounds are also possible. These compounds have, in addition to the aforementioned ethylenically unsaturated residues, no further ethylenically unsaturated residues such as, for example, vinyl ether groups and/or (meth)acrylate groups. Salts containing allyl and/or methallyl residues are precluded as component b).

The allyl and/or methallyl residues in the compounds of ingredient b) are preferably allyl ether and/or methallyl ether residues.

Particularly preferred, ingredient b) is a compound represented by Formula III

(III), in which $R^7$ is an m-valent residue, that has perhaps one or several substituents, $R^8$ is a group $CH_2-CR^9=CH_2$, $R^9$ means hydrogen or methyl, m is a whole number from 1 to 12, preferably 1 to 8, particularly preferred 1 to 6, and most particularly preferred 1 to 4, and Y is selected from the group of covalent bonds or a bivalent residue.

Compounds represented by Formula III can be used as individual compounds or as mixtures of various compounds represented by Formula III. Particularly for higher-functioning compounds with three or more (meth)allyl groups, mixtures consisting of various compounds represented by Formula III with different degrees of functionality can be used. One example of this are technical mixtures consisting of (meth)allyl pentaerythritol ethers with various degrees of functionalization.

If the aforementioned Formula III refers to m-valent $R^7$ residues, these can be any monovalent to 12-valent residues.

The m-valent residues $R^7$ can, for example, be aliphatic, cycloaliphatic, aromatic, araliphatic or hetero-cyclic residues, in which one to twelve bonds are available for bonding with the Y residue or $R^8$. Examples for monovalent or bivalent residues of this type can be found in the above sections in the description of the alkyl, cycloalkyl, aryl, aralkyl, heterocyclyl, alkylene, alkylene ether, cycloalkylene, arylene, aralkylene and heterocyclene residues. Higher-valent $R_7$ residues where, for example, m=3 or 4 have the corresponding structures, but with additional free valences for bonding with Y or $R^8$.

Examples of $R^7$ residues with higher valency in which, for example, m=2 to 12, are polysiloxane, in which 2 to 12 silicon atoms are functionalized with allyl or methallyl groups or with allyl ether or methallyl ether groups; or carbohydrates in which 2 to 12 hydroxy groups are etherified with allyl or methallyl groups, or polyvinyl alcohols, in which 2 to 12 hydroxy groups are functionalized with allyl or methallyl groups.

Examples for (meth)allyl compounds with more than four allyl groups are polyalkyl compounds in the form of unsaturated polyesters with allylic and/or methallylic side chains, in particular, mixtures of these polyesters that do not contain styrol.

Examples of (meth)allyl compounds having six allyl groups and/or methallyl groups are mannitol hexaallyl ether, sorbitol hexyallyl ether or inositol hexaallyl ether, as well as the corresponding methallyl derivatives.

Examples of (meth)allyl compounds with more than six allyl groups and/or methallyl groups are polysaccharides with more than six allyl groups and/or methallyl groups.

The m-valent $R^7$ residues can also be further residues in which one to twelve bonds are available for connecting with the Y residue or with $R^8$. Examples of further residues are urea, cyanamide, phosphonate, carbonate, cyanurate, isocyanurate, pyrocarbonate, monoalkylsilane, dialkylsilane, trialkylsilane, monoarylsilane, diarylsilane, triarylsilane, tetrealkyldisiloxane, tetraaryldisiloxane, tetrakis(trialkylsiloxy) disiloxane, thiourea, sulfide, sulfone, borane, phosphate, phosphite and thiourea residues. Preferably, these have one to two allyl groups or methallyl groups.

The m-valent organic $R^7$ residues can, if appropriate, be substituted, for example, with one or more alkyl, alkoxy, amino or hydroxy residues or with one or more halogen atoms, for example chloride atoms, or with combinations of two or more of these substituents.

For $R^7$ residues with higher valency, not all functionalities have to be connected with $R^8$ residues. It is certainly possible that only some of these functional groups are connected with such residues and that the remaining functional groups are not derived or connected with other saturated residues and/or with residues derived from maleic acid or fumaric acid (derivatives fixtures consisting of various ingredients b) can also be used.

In addition to the previously described substituents, $R^7$ can also contain acid functions such as for example, phosphoric acid groups, phosphonic acid groups, sulfonic acid groups and/or carboxylic acid groups as well as their anhydrides. Dental masses having compounds containing such free acid groups are particularly suited for use as self-etching dental cements.

The following compounds (R=H or methyl) are examples of the use of particularly preferred reactive paste-forming agents b) with acid functions according to the invention:

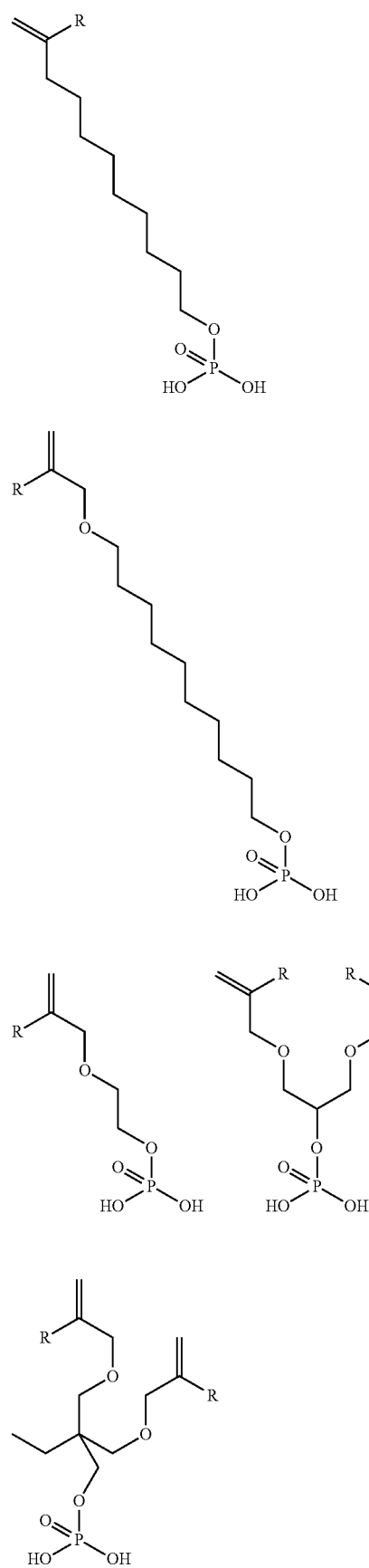

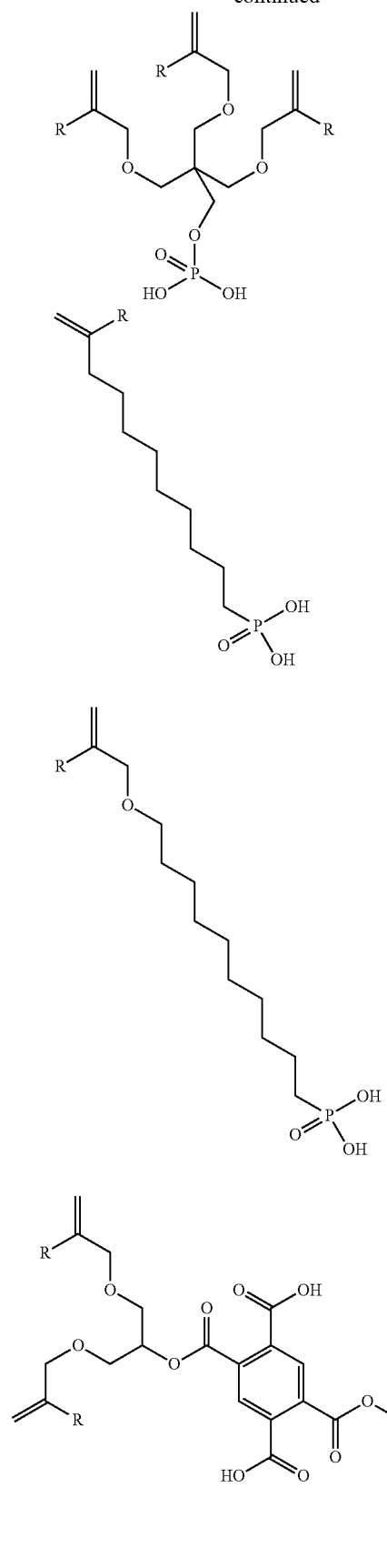

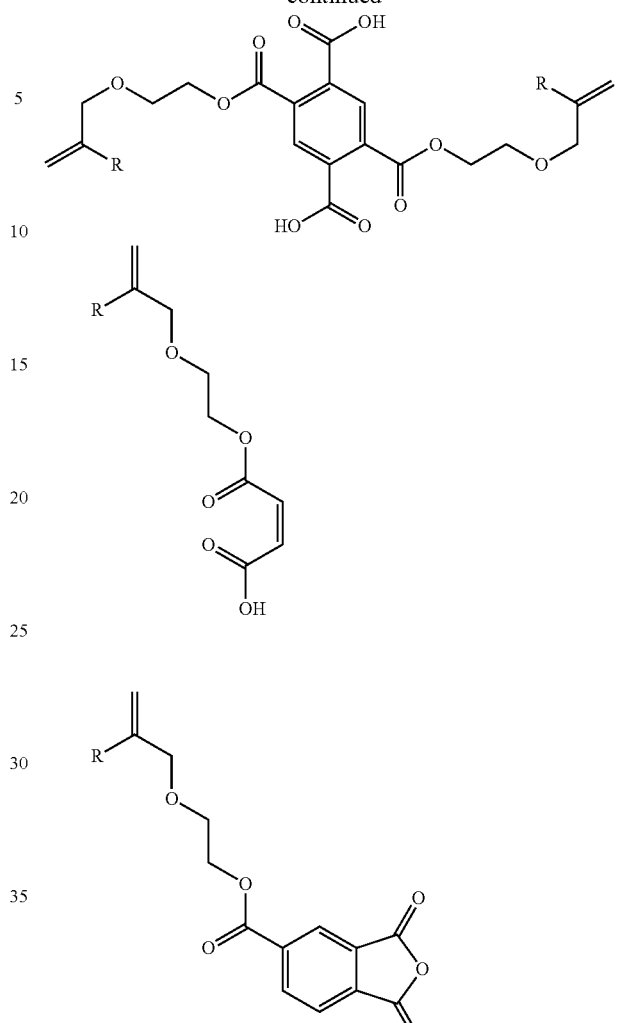

It can be expedient, particularly also in this context, if the reactive paste-forming agents b) preferably used according to the invention also have free hydroxyl groups at substituent $R^7$ in addition to the acid function and/or if mixtures of acid-functionalized reactive paste-forming agents b) with hydroxyl-functionalized reactive paste-forming agents b) are used.

Examples of hydroxyl-functionalized reactive paste-forming agents b) that are particularly preferred according to the invention are the following compounds (R=H or methyl):

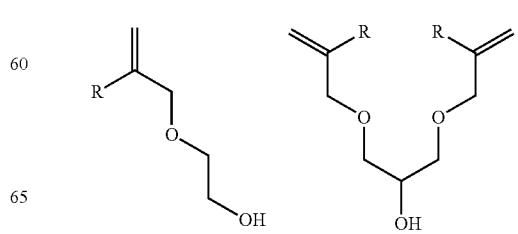

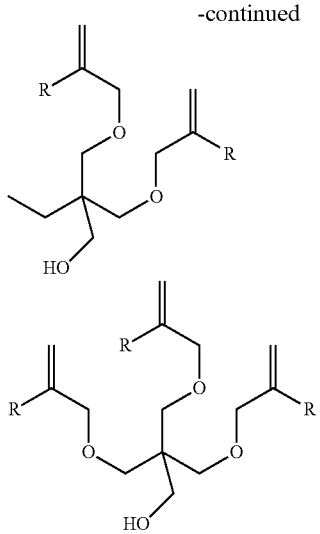

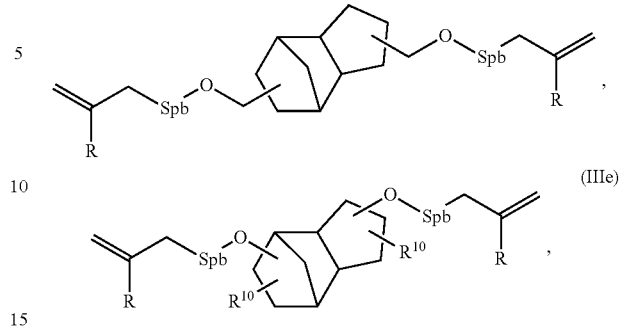

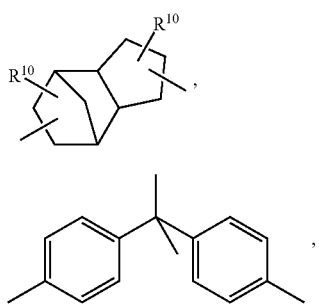

If reference is made to Y as bivalent residue in the aforementioned Formula these can be any bivalent organic or inorganic residues. Y can be any bridge group or a covalent bonding that connects the $R^7$ and $R^3$ with each other.

Examples of bivalent Y residues are the perhaps substituted, bivalent residues, i.e. alkylene, alkylene ether, cycloalkylene, arylene, aralkylene and heterocyclene enumerated above. Further examples for bivalent Y residues are carboxylic acid, carboxylic acid ester, carboxylic acid amide or amide groups as well as oxygen or sulfur atoms.

Examples of particularly preferred reactive paste-forming agents b) according to the invention are compounds represented by the Formula IIIa:

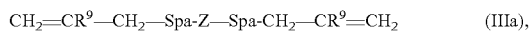

in which $R^9$ is hydrogen or methyl,

Spa is a covalent bond between 2 C atoms or a bivalent bridge group, preferably an oxygen atom, an amino group, alkylene, alkylene glycol ether, cycloalkylene, arylene, aralkylene or heterocyclylene, and Z is a bivalent polycyclic residue or a bivalent mononuclear or binuclear residue, preferably a residue represented by the following Formulas IIIb or IIIc:

(IIIb)

(IIIc)

wherein $R^{10}$ is hydrogen, hydroxyl, alkoxy or amino, in particular $NH_2$.

Examples of particularly preferred reactive paste-forming agents b) according to the invention are represented by Formula IIId and Formula IIIe:

in which R is hydrogen or methyl,

Spb is a covalent bond between a C atom and an O atom, or represents a bridge group, preferably alkylene, alkylene glycol ether, cycloalkylene, arylene, aralkylene or heterocyclylene, and $R^{10}$ is hydrogen or a hydroxy, alkoxy or amino residue.

Most particularly preferred examples of the compounds represented by Formula IIId are compounds represented by the following formula:

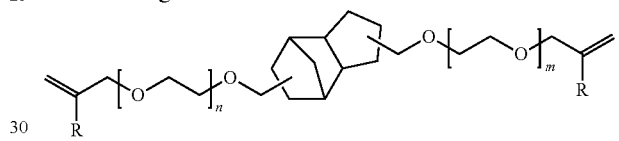

where n=0, 1, 2, . . . 15 and m=0, 1, 2, . . . 15 and R=hydrogen or methyl.

Most particularly preferred examples of the compounds represented by Formula IIIe are compounds represented by the following Formula:

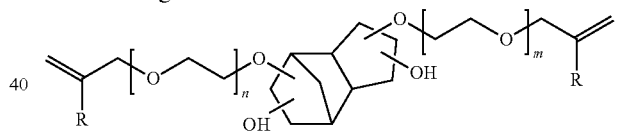

where n=0, 1, 2, . . . 15 and m=0, 1, 2, . . . 15 and R=hydrogen or methyl, whereby the (meth)allyl ether groups and the hydroxyl groups are preferably respectively attached to the adjacent carbon atoms on the benzene ring.

Alternative to the compounds that have been illustrated having ethylene glycol units [—O—CH₂—CH₂—]$_n$ preferably, compounds having propylene glycol units [—O—CH₂—CH(CH₃)—]$_n$ or having butylene glycol, such as tetramethylene glycol units, [—O—CH₂—CH₂—CH₂—CH₂—]$_n$ or having cyclopentylene units [—O—C₅H₈—]$_n$ or having cyclohexylene units [—O—C₆H₁₀—]$_n$ or having phenylene units [—O—C₆H₄—]$_n$ or having naphthylene units [—O—C₁₀H₆—]$_n$ or having benzylene units [—O—CH₂—C₆H₄—]$_n$ can be used, whereby n can be a whole number from 1 to 15. This correspondingly applies to ethylene glycol units [—O—CH₂—CH₂—]$_m$.

Further examples of particularly preferred reactive paste-forming agents b) according to the invention are the compounds represented by the following formulas:

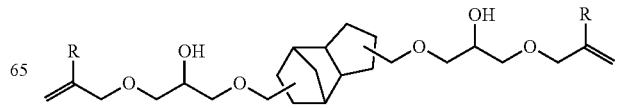

-continued
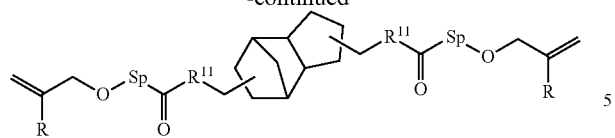
where
Sp=bridge group, preferably alkylene or alkylene glycol ether,
R=hydrogen or methyl, and
$R^{11}$=oxygen atom or an —NH group.
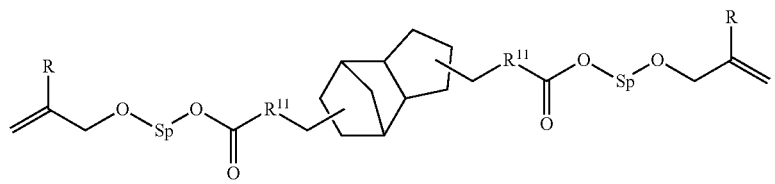
where
Sp=bridge group, preferably alkylene or alkylene glycol ether,
$R^{11}$=oxygen atom or an —NH group, and
R=hydrogen or methyl.
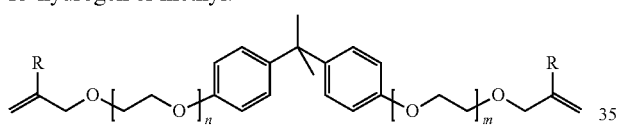
where n=0, 1, 2, . . . 15 and m=0, 1, 2, . . . 15 and R=hydrogen or methyl.
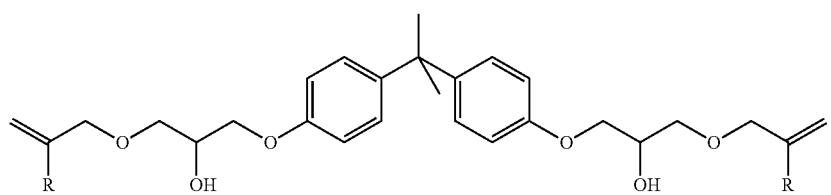
where R=hydrogen or methyl.
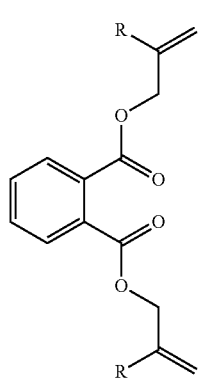
-continued
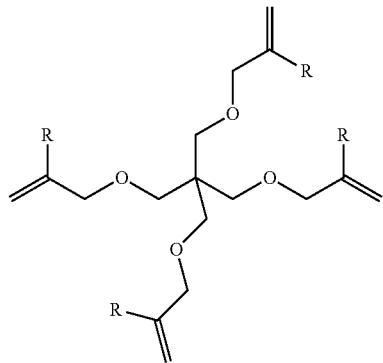

where R=H, alkyl, in particular methyl. Thereby, the pentaerythritol ether can preferably be used as technical mixture of the quadruple-functionalized ether with low-functionalized ethers, for example, as technical mixture containing the quadruple, triple and bi-functionalized pentaerythritol ether.

Further examples for particularly preferred reactive paste-forming agents b) according to the invention are the following compounds:

Diallyl malate, diallyl urea, N,N-diallylacrylic amide, diallyl sebacate, diallyl terephthalate, diallyl malonate, diallyl oxalate, diallyl cyanamide, diallyl glutarate, diallyl diglycolate, diallyl fumarate, diallyl homophthalate, diallyl ether, diallyl itaconate, diallyl allylphosphonate, diallyl suberate, diallyl succinate, N,N-diallyl(meth)acrylamide, diallyl isophthalate, diallyl maleate, diallyl azelate, diallyl carbonate, trimethylolpropane diallyl ether, glycerin-α,α'-diallyl ether, isocyanuric acid diallyl-n-propylester, isocyanuric acid diallyl ester, pyrocarbocylic diallyl ester, diethyl diallylmalonate, diallyl phthalate, diallyl diphenylsilane, 1,3-diallyltetra-methyldisiloxane, diallyl dimethylsilane, 1,3-diallytetrakis(trimethylsiloxy)disiloxane, diallyl maleate, N,N'-diallylthiourea, diallyl sulfide, diethyl-2,2-diallylmalonate, diallyl sulfone, diallyl adipate ($C_{12}H_{18}O_4$), 1,2-diallyl-cyclohexane-1,4-dicarboxylate ($C_{14}H_{20}O_4$; cis-/transmixture), trialkylborane, triallyl phosphate, triallyl trimesate, triallyl aconitate, triallyl citrate, triallyl isocyanurate, pentaerythritol triallyl ether, triallyl cyanurate, triallyl phosphite, triallyl thiourea, triallyl trimellitate, isocyanuric acid triallyl ester, tetraallyl pyromellitate, 1,1,3,3-tetraallyloxypropane, tetraallyl pentaerythritol and tetraallyl oxyethane or the analog methallyl compounds.

Within the scope of the present description, barbituric acid derivatives c) refer to barbituric acid, thiobarbituric acid and particularly substituted barbituric acids and substituted thiobarbituric acids. Salts of barbituric acid and their derivatives,
as well as thiobarbituric acid and its derivatives are precluded.

Even salts of malonyl sulfamides are precluded.

Ingredient c) can be any barbituric acid derivative and/or malonyl sulfamide. In addition to barbituric acid, even its derivatives, preferably the compounds substituted in the 1, 3 and/or 5 position, or the corresponding thiobarbiturates can be used. Particularly preferred, these are barbituric acid derivatives represented by Formula IV or V or malonyl sulfamides represented by Formula VI

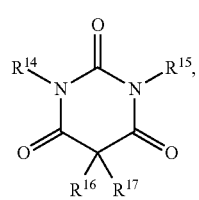

(IV)

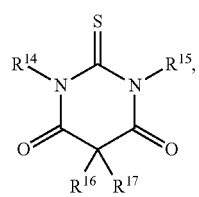

(V)

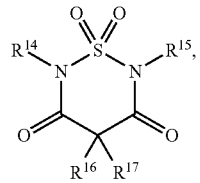

(VI)

in which $R^{16}$ and $R^{17}$, independent of each other, mean hydrogen, alkyl, alkenyl, cycloalkyl, aryl, aralkyl and heterocyclyl, provided that at least one of the residues $R^{16}$ or $R^{17}$ means hydrogen, and
$R^{14}$ and $R^{15}$, independent of each other, mean hydrogen, alkyl, alkenyl, cycloalkyl, aryl, aralkyl and heterocyclyl.

Most particularly preferred are barbituric acid derivatives represented by Formula IV, in which $R^{14}$ and/or $R^{16}$ or $R^{17}$, independent of each other, mean alkyl, cycloalkyl, aryl or aralkyl, in particular ethyl, butyl, phenyl or benzyl.

Examples of particularly preferred polymerization initiators c) according to the invention are the barbituric acids and barbituric acid derivatives described in DE 1 495 520, and the malonyl sulfamides described in EP 0 059 451 B1.

Preferred malonyl sulfamides are 2,6-dimethyl-4-isobutyl-malonyl sulfamide, 2,6-diisobutyl-4-propylmalonyl sulfamide, 2,6-dibutyl-4-propylmalonyl sulfamide, 2,6-dimethyl-4-ethyl-malonyl sulfamide and 2,6-dioctyl-4-isobutylmalonyl sulfamide.

Examples of particularly preferred barbituric acid derivatives are 1-benzyl-5-phenylbarbituric acid, 1-cyclohexyl-5-ethylbarbituric acid, 1,3-dimethyl-5-cyclopentylbarbituric acid, 1,3-dimethyl-5-cyclohexylbarbituric acid, 1,3-dimethyl-5-ethylbarbituric acid, 1,3-dimethyl-5-isobutylbarbituric acid, 1,3-Dimethyl-5-phenylbarbituric acid, 1,3-dimethyl-5-n-butylbarbituric acid, 1,5-dimethylbarbituric acid, 5-n-butylbarbituric acid, 5-cyclohexylbarbituric acid, 5-ethylbarbituric acid, 5-isobutylbarbituric acid, 5-isopropylbarbituric acid, 5-phenylbarbituric acid and 1,3,5-trimethylbarbituric acid. These barbituric acid derivatives can be used by themselves or as a mixture of two or several.

If the Formulas I to VI listed above refer to alkyl residues, these are saturated, branched or unbranched aliphatic hydrocarbon residues. As a rule, the length of their chain is up to 10 C atoms. Preferred are $C_1$ to $C_8$ alkyl residues. Examples are methyl, ethyl, n-propyl, isopropyl, n-butyl, sec-butyl, tert-butyl, n-pentyl, n-hexyl or 2-ethylhexyl. Where appropriate, alkyl residues can be substituted, for example, with one or several alkoxy, amino or hydroxy residues or with acidic residues such as, for example, phosphoric acid groups, phosphonic acid groups, sulfonic acid groups and/or carboxylic acid groups and their anhydrides, or with one or several halogen atoms, for example, chloride atoms, or with combinations of two or more of these substituents.

If the Formulas IV to VI listed above refer to alkenyl residues, these are simply unsaturated, branched or unbranched aliphatic hydrocarbon residues. As a rule, they have a chain length of up to 10 C atoms. $C_2$ to $C_8$ alkenyl residues are preferred. Examples of this are allyl, methallyl or vinyl. Alkenyl residues can, if appropriate, be substituted, for example, with one or more alkoxy, amino or hydroxy residues or with acidic residues such as, for example, with phosphoric acid groups, phosphonic acid groups, sulfonic acid groups and/or carboxylic acid groups and their anhydrides, or with one or several halogen atoms, for example, chloride atoms or with combinations of two or more of these substituents.

If the Formulas I to VI listed above refer to cycloalkyl residues, these are saturated cycloaliphatic hydrocarbon residues. As a rule, these have five to eight carbon atoms on the benzene ring. Preferred are cyclopentyl or in particular, cyclohexyl residues. These residues can also have one or more cycloalkyl rings. Several cycloalkyl rings can be interlinked with each other by covalent bonds or bridge groups or form bi or polycyclic ring systems. Cycloalkyl residues can, if appropriate, be substituted, for example, with one or more alkyl, alkoxy, amino or hydroxy residues or with acidic residues such as, for example, with phosphoric acid groups, phosphonic acid groups sulfonic acid groups and/or carboxylic acid groups and their anhydrides, or with one or more halogen atoms, for example, chloride atoms, or with combinations of two or more of these substituents.

If the Formulas I to VI listed above refer to aryl residues, these are aromatic hydrocarbon residues. As a rule, these have six to twelve carbon atoms on the benzene ring. Preferred are naphthyl, or in particular, phenyl residues. Several aryl rings can be interlinked with each other by covalent bonds or bridge groups, or form bi or polycyclic aromatic ring systems. Aryl residues can, if appropriate, be substituted, for example, with one or more alkyl, alkoxy, amino or hydroxyl residues or with acidic residues such as, for example, with phosphoric acid groups, phosphonic acid groups sulfonic acid groups and/or carboxylic acid groups and their anhydrides, or with one or more halogen atoms, for example, chloride atoms, or with combinations of two or more of these substituents.

If the Formulas I to VI listed above refer to aralkyl residues, these are aromatic hydrocarbon residues bonded with an alkylene residue. As a rule, these residues have six to twelve carbon atoms on the benzene ring and one to three carbon atoms in the alkylene residue. Benzyl is a preferred example of an aralkyl residue. If appropriate, aralkyl residues can be substituted, for example, with one or more alkyl, alkoxy, amino or hydroxy residues, or with acidic residues such as, for example, phosphoric acid groups, phosphonic acid groups, sulfonic acid groups and/or carboxylic acid groups and their anhydrides, or with one or more halogen atoms, for example, chloride atoms, or with combinations of two or more of these substituents.

If the Formulas I to VI listed above refer to alkylene residues, these are saturated branched or unbranched bivalent aliphatic hydrocarbon residues. As a rule, these have a chain length of up to 8 C atoms. Preferred are $C_1$ to $C_6$ alkyl residues. Examples are methylene, ethylene, n-propylene, iso-propylene, n-butylene, sec.-butylene, tert.-butylene, n-pentylene and n-hexylene. If appropriate, alkylene residues can be substituted, for example, with one or more alkoxy, amino or hydroxy residues, or with acidic residues such as, for example, with phosphoric acid groups, phosphonic acid groups, sulfonic acid groups and/or carboxylic acid groups and their anhydrides, or with one or more halogen atoms, for example, chloride atoms, or with combinations of two or more of these substituents.

If the Formulas I to VI listed above refer to alkylene glycol ether residues, these are residues that are derived from saturated branched or unbranched aliphatic alkylene glycols. These residues can have one or more repeating structural units. As a rule, the alkylene units have two to four carbon atoms. Examples of residues of this type are $—[C_2H_4—O]_q—C_2H_4—$, $—[C_3H_6—O]_q—C_3H_6$-und $—[C_4H_8—O]_q—C_4H_8—$ where q=1-100, preferably 1-30, in particular, 1-15. Alkylene glycol ether residues can, if appropriate, be substituted, for example, with one or more alkoxy, amino or hydroxyl residue or with one or more halogen atoms, for example, chloride atoms, or with combinations of two or more of these substituents.

Ingredient d) can be any organic compound having at least one acrylic acid ester and/or methacrylic acid ester residue. In addition to monomeric compounds, oligomeric and polymeric (meth)acrylates are also suitable, provided these still have (meth)acrylic ester groups that are able to polymerize. Particularly preferred, these are compounds represented by Formula VII:

(VII)

in which p is a whole number from 1 to 12, preferably 1 to 4, $R^{12}$ is a p-valent organic residue that has perhaps one or more substituents, and
$R^{13}$ means hydrogen or methyl.

If the above Formula VII refers to a p-valent organic residue $R^{12}$, this can be any monovalent to twelve-valent organic residue.

P-valent organic residues $R^{12}$ can be aliphatic, cycloaliphatic, aromatic, araliphatic or heterocyclic residues in which one to twelve bonds are available for connecting with the (meth)acrylate residue. Examples for such monovalent or bivalent residues $R^{12}$ can be found in the above sections in the description of the alkyl, cycloalkyl, aryl, aralkyl, heterocyclyl, alkylene, alkylene ether, cycloalkylene, arylene, aralkylene and heterocyclylene residues. Higher-valent residues where p=3 to 12 have corresponding structures, however, with more free valences for bonding with the (meth) acrylate group(s). Alternatively, the p-valent organic residues can also be residues of any polymer that is, for example, functionalized with 1-6 (meth)acrylate groups.

Examples for higher-valent $R^{12}$ residues where, for example, m=2 to 12, are polysiloxanes, in which 2 to 12 silicon atoms are functionalized with acrylate or methacrylate groups; or hydrocarbons in which 2 to 12 hydroxy groups are esterified with acrylate or methacrylate groups, or polyvinyl alcohols, in which 2 to 12 hydroxy groups are functionalized with acrylate or methacrylate groups.

In multi-valent organic residues $R^{12}$, not all functionalities have to be bonded with (meth)acrylate residues. It is certainly possible that only some of these functional groups are connected with such residues and that the other functional groups are not derivatives, or are connected with other saturated and/or unsaturated residues. Even mixtures of various ingredients d) can be used.

The p-valent organic residues $R^{12}$ can, if appropriate, be substituted, for example, with one or more alkyl, alkoxy, amino or hydroxy residues, or with acidic residues such as, for example, with phosphoric acid groups, phosphonic acid groups, sulfonic acid groups and/or carboxylic acid groups and their anhydrides, or with one or more halogen atoms, for example, chloride atoms, or with combinations of two or more of these substituents.

Examples for preferably used (meth)acrylate compounds d) are at least bifunctional acrylic acid and/or (meth)acrylic acid esters. These can be monomeric or polymeric acrylates and methacrylates. For example, the long-chained monomers of U.S. Pat. No. 3,066,112 can be used advantageously on the basis of bisphenol-A and glycidyl(meth)acrylate or their derivatives created by the addition of isocyanates. Particularly suited are also compounds of the type bisphenol-A-diethyloxy(meth)acrylate and bisphenol-A-dipropyloxy (meth)acrylate. Furthermore, preferably oligo-ethoxylated and oligo-propoxylated bisphenol-A-diacrylic and di(meth) acrylic acid ester can be used.

Also well suited are, acrylic acid and methacrylic acid diester or higher esters of at least bifunctional aliphatic alcohols, for example, triethylene glycol di(meth)acrylate, ethylene glycol-di(meth)acrylate, hexanediol di(meth)acrylate or trimethylolpropane-tri(meth)acrylate.

Particularly suitable are also the diacrylic and dimethacrylic acid esters of bis(hydroxymethyl)-tricyclo [5.2.1.0$^{2,6}$]decane and the diacrylic and di(meth)acrylic acid ester of the compound bis(hydroxymethyl)tricyclo [5.2.1.0$^{2,6}$]decane that is extended with the 1 to 3 ethylene oxide and/or propylene oxide units cited in DE 28 16 823 C2.

Well suited monomers d) are also the (meth)acrylic acid esters, e.g. triglycolic acid bis[3(4)-(meth)acryloxymethyl-8 (9)-tricyclo[5.2.1.0$^{2,6}$]decylmethylester] described in EP 0 235 826 A1.

Of course, mixtures consisting of monomers and/or unsaturated polymers produced from such can also be used.

In a further preferred embodiment, in addition to at least bifunctional acrylic acid and methacrylic acid esters up to 70%, relative to ingredient d), preferably up to 50% monofunctional (meth)acrylic acid esters such as methyl(meth) acrylate, can be used.

Further preferred examples of (meth)acrylates d) include: methyl(meth)acrylate, ethyl(meth)acrylate, isopropyl(meth) acrylate, n-butyl(meth)acrylate, isobutyl(meth)acrylate, hydroxypropyl(meth)acrylate, tetrahydrofurfuryl(meth) acrylate, glycidyl(meth)acrylate, 2-hydroxyethyl(meth)acrylate, 2-hydroxypropyl(meth)acrylate, 3-hydroxypropyl (meth)acrylate, 2-methoxyethyl-(meth)acrylate, 2-ethoxyethyl(meth)acrylate, 2-methoxyethyl(meth)acrylate, 2-ethylhexyl(meth)acrylate, benzyl(meth)acrylate, 2-hydroxy-1,3-di(meth)acryloxypropane; neopentyl glycol di(meth)acrylate, 1,3-butanediol di(meth)acrylate, 1,4-butanediol di(meth)acrylate, 1,6-hexanediol di(meth)acrylate, 1,8-octanediol di(meth)acrylate, 1,10-decanediol di(meth) acrylate, 1,12-dodecanediol di(meth)acrylate, 1,14-tetra-decanediol di(meth)acrylate, 1,16-hexadecanediol di(meth) acrylate, trimethylolpropane tri(meth)acrylate, trimethylolethane tri(meth)acrylate, pentaerythritol tri(meth) acrylate, trimethylolethane tri(meth)acrylate, pentaerythritol tetra(meth)acrylate, bisphenol-A-diglycidyl(meth)acrylate, mono oder polyethylene glycol di(meth)acrylate, e.g. ethylene glycol di(meth)acrylate, diethylene glycol di(meth)acrylate and triethylene glycol di(meth)acrylate, mono- or polypropylene glycol di(meth)acrylate, and mono or polybutylene glycol di(meth)acrylate, e.g. polytetrahydrofuran di(meth)acrylate, whereby the polyethylene glycol, polypropylene glycol and polybutylene glycol or polytetramethylene glycol derivatives include those with branched as well as those with a linear structure.

Further, examples of the (meth)acrylates with urethane bond(s) include di-2-(meth)acryl-oxyethyl-2,2',4-trimethylhexamethylene dicarbamate, di-2-(meth)acryl-oxyethyl-2,4, 4'-trimethylhexamethylene dicarbamate and 1,3,5-tris[1,3-bis{(meth)-acryloyloxy}-2-propoxycarbonylaminohexane]-1,3,5-(1H,3H,5H)triazin-2,4,6-trion. Additionally, by way of example a (meth)acrylate of a urethane oligomer is cited that has 2,2'-di(4-hydroxycyclohexyl)propane, 2-oxepanon, hexamethylene diisocyanate and 2-hydroxyethyl(meth)acrylate, and a (meth)acrylate of a urethane oligomer that has 1,3-butanediol, hexamethylene diisocyanate and 2-hydroxyethyl (meth)acrylate. These (meth)acrylates can be used by themselves or as a mixture of two or more.

Preferred are ingredients d) that contain tetrahydrofurfuryl (meth)acrylate, glycidyl(meth)acrylate, 2-hydroxyethyl (meth)acrylate, 2-hydroxypropl(meth)acrylate, 3-hydroxypropyl(meth)acrylate and 2-hydroxy-1,3-di(meth)acrylate. Because they easily dissolve barbituric acid derivatives or malonyl sulfamide and organic halides, the aforementioned compounds are preferably contained in ingredient d).

The dental material according to the invention further contains metal compounds in component B as ingredient e).

Ingredient e) can be any metal compound. These are used as catalysts for the formation of free radicals. As a rule, metal salts and/or metal complexes are used.

The metals of ingredient e) are generally metals of the third and fourth main group and the first to eighth secondary group of the periodic table of the elements, including the lanthanides. These metal compounds are preferably used as salts or complex compounds of copper, iron, tin, chromium, manganese, cobalt, zinc, nickel, the rare earth metals and aluminum.

The metals can be present in various non-negative oxidation states, for example, in oxidation state +1 or particularly +2. Metals of ingredient e) can also be present in different oxidation states, or mixtures of various metal compounds can be used.

The metal salts can have any kind of anion. Examples of anions are halides, pseudo-halides, sulfates, sulfonates, phosphates, phosphonates and particularly carboxylates, such as anions of aliphatic or aromatic carboxylic acids, for example, (meth)acrylic acid anions.

The metal complexes can have any ligands. Examples of ligands are any Lewis bases that can form coordinative bonds with the metal atoms. Preferably used as ligands in ingredient e) are metal complexes with carbonyl compounds and/or with nitrogen atoms, particularly preferred with beta-carbonyl compounds, most particularly preferred, with acetylacetonate.

Examples of preferred metal complexes or metal salts of ingredient e) are copper acetylacetonate, copper-4-cyclohexylbutyrate, copper acetate, copper oleate, copper ethylhexanoate, copper acrylate, copper methacrylate, copper naphthenate, manganese acetylacetonate, manganese naphthenate, manganese octylate, cobalt acetylacetonate, cobalt naphthenate, zinc acetylacetonate, zinc naphthenate, nickel acetylacetonate, nickel acetate, chrome acetylacetonate, iron acetylacetonate, sodium naphthenate and rare earth octoate.

Metal compounds of ingredient e) can be used by themselves or in a mixture of two or more.

Preferably used ingredients e) are metal compounds that are present in dissolved form in component B, in particular in the form of dissolved organic compounds. As metal, copper is particularly suitable.

Further, in component B, the dental material according to the invention contains halide or pseudo-halide compounds as ingredient 0.

Ingredient f) can be any halide or pseudo-halide compounds that are used in the form of soluble salts in component B.

Salts are considered to be soluble salts if they dissolve to at least 1 g per liter at 25° C. in organic compound d).

In general, halide compounds are fluorides, chlorides, bromides or iodides.

Pseudo-halide compounds are generally compounds having the anions $CN^-$, $N_3^-$, $OCN^-$, $NCO^-$, $CNO^-$, $SCN^-$, $NCS^-$ or $SeCN^-$.

As cations, generally any metal cation, preferably, however, the metal cations of metals of the first and the second main group of the periodic table, in particular, potassium, sodium and lithium cations come into consideration; or also ammonium or phosphonium cations, in particular, those with organic residues, including the hydrohalides of amines, in particular of tertiary amines.

Preferred ingredients f) are halides, in particular chloride or bromide, or pseudo-halides of the metals of the first or the second main group of the periodic table of the elements, in particular, lithium or sodium, or the quaternary ammonium ions, the quaternary phosphonium ions and hydro-halides of tertiary amines.

Examples of preferred ingredients f) are organic halides such as benzyltributyl ammonium chloride, benzyldimethylcetyl ammonium chloride, benzyldimethylstearyl ammonium chloride, benzyltriethyl ammonium bromide, benzyltrimethyl ammonium chloride, cetylalkonium chloride, cetylpyridinum bromide, cetylpyridinum chloride, cetyltriethyl ammonium bromide, mono to tetraallylalkyl ammonium chloride, mono to tetraallylalkyl ammonium bromide, particularly diallyldimethyl ammonium chloride, dodecyldimethyl ammonium chloride, dilauryldimethyl ammonium chloride, lauryldimethyl ammonium chloride, tetra-n-butyl ammonium bromide, tetra-n-butyl ammonium chloride, tetradecyltrimethyl ammonium bromide, tetraethyl ammonium bromide and trioctylmethyl ammonium chloride, the corresponding phosphonium compounds or hydro-halides of tertiary amines, in particular the hydrochloride of tertiary amines.

The compounds of ingredient f) can be used alone or in a mixture of two or more.

In a preferred embodiment, the multicomponent composition according to the invention contains in at least one component at least one filler g). In particular, component B contains at least one filler g), or components A and B respectively contain at least a filler g).

The fillers (ingredient g)) are inorganic or organic materials. Examples of inorganic materials are silicone dioxide in its various modifications (such as, for example, quartz, cristobalite, fused silica), feldspar, ground glass such as barium glass, alumina glass, potassium glass and fluoro-alumino silicate glass, and slightly soluble fluorides such as, $CaF_2$, $YF_3$, $YbF_3$, moreover silica gels and silica, in particular, pyrogenic silica or its granulates, or synthetic zeolite, calcium phosphate, aluminum silicate, calcium silicate, magnesium carbonate, hydrated calcium silicate or hydrated aluminum silicate (kaolin). These fillers can be subjected to a surface treatment, for example, with γ-(meth)acryloxypropyl trimethoxysilane, vinyltrichlorosilane, vinyltriethoxysilane, vinyltrimethoxysilane, vinyltriacetoxysilane, vinyltri(methoxyethoxy)silane, alkyltrichlorsilane, alkyltriethoxysilane, alkyltrimethoxysilane, alkyltriacetoxysilane, alkyltri(methoxyethoxy)silane, in particular, methyltrichlorosilane, methyltriethoxysilane, methyltrimethoxysilane, methyltriacetoxysilane and methyltri(methoxyethoxy)silane. Further, applicable organic/inorganic composite fillers can be produced by mixing the above fillers with a polymerizable monomer or oligomer, hardening of the mixture and subsequent pulverization of the hardened mixture.

Completely pigmented polymethyl(meth)acrylate pearls are also suitable as filler, or other pulverized organic polymerizates. To increase the flexibility of the dental masses it can also be advantageous to use soluble organic polymers. Suitable are, for example, polyvinyl acetate and copolymers on the basis of vinylchloridivinyl acetate, vinylchloridivinyl isobutyl ether and vinyl acetate/maleic acid dibutyl ether.

The fillers can be used by themselves or in a mixture of two or several. The maximum average grain size of the inorganic fillers is preferably 15 μm, in particular 10 μm. Most particularly preferred, fillers with an average grain size of <5 μm are used.

For the fillers, component parts of silica anhydride, silica, hydrated calcium silicate and hydrated aluminum silicate (kaolin) are preferred, because these, even when stored for long periods of time, ensure that the paste-like polymerizable dental material does not gel. For the remainder, depending on the reactive paste-forming agents a) and/or b), various fillers g) can be used in the corresponding pastes.

To realize a higher monomer conversion it is further advantageous if the polymerizable dental material contains, as ingredient h), an organic peroxide compound of up to 5% by weight relative to the total mass of component A and/or B that contains ingredient h). Preferably, ingredient h) is contained in component A. Preferably, ingredient h) is a carboxylic acid peroxyester, carbon dioxide peroxyester, diacyl peroxide, perketal, peracetal, perether, hydroperoxid, a peracid, or a combination or two or more of such. Thereof, carboxylic acid peroxyester, carbon dioxide peroxyester and perketals are particularly preferred. Most particularly preferred, tert-butylperoxy-3,5,5-trimethyl-hexanoate, tert-butylperoxybenzoate, tert-butylperoxy-2-ethylhexylcarbonate or combinations of two or more of such are used.

If the dental material according to the invention contains organic peroxide h), a metal compound e), a halide or pseudo-halide f) and an initiator c) (barbituric acid derivatelmalonyl sulfamide), it is then particularly expedient if the organic peroxide h), the initiator c) and the combinations of metal compound e) and halide or pseudo-halide f) are present in two spatially separate components. For example, the organic peroxide h), the reactive paste-forming agents a) and/or b) according to the invention, an initiator c) (barbituric acid derivateimalonyl sulfamide) and fillers g) can be kneaded into a paste. On the other hand, the polymerizable monomers d) can also be present together with a combination of metal compound e) and halide or pseudo-halide f) and fillers g).

Beyond that, the dental masses according to the invention can contain one or more additives i), which are customarily added to these types of masses. Examples of such are buffer salts, water scavengers such as, for example, zeolite, carboxylic acid anhydrides such as acetic acid anhydride, succinic acid anhydride, phthalic acid anhydride and maleic acid anhydride and/or dehydrated salts to prevent hydrolysis and transesterification reactions, metal scavengers such as Quadrapure®, metal complex-forming agents such as, for example, EDTA, additional paste-forming agents, tensides, active ingredients, substances making optical scanning possible, flavoring substances and/or odorants, substances making diagnostics possible, dental substance (enamel, dentin), substances with etching and/or adhesive effect, fluoridation agents, bleaching substances, desensitization agents, adhesive composite agents, colorants, pigments, indicators, other initiators different from components c), e), f) and h), or indicator components such as, for example, inorganic peroxides, inorganic peracids or their peresters or redox initiator components and/or photo initiators, stabilizers (such as antioxidants), polymerization inhibitors, thixotropy aids and antibacterial substances.

As a rule, the proportion of ingredient a) in component A is 10-85% by weight, preferably 20-80% by weight, particularly preferred, 30-75% by weight.

As a rule, the proportion of ingredient b) in component A is 10-85% by weight, preferably 20-80% by weight, and particularly preferred, 30-75% by weight.

As a rule, the proportion of ingredient c) in component A is 0.5-20% by weight, and preferably 2-10% by weight.

As a rule, the proportion of ingredient h) in component A is 5% by weight, and preferably up to 2% by weight.

As a rule, the proportion of ingredient d) in component B is 20-85% by weight, preferably 25-80% by weight, particularly preferred, 30-75% by weight.

As a rule, the proportion of ingredient e) in component B is 1-100 ppm, and preferably 2-50 ppm.

As a rule, the proportion of ingredient f) in component B is 0.01-1% by weight, and preferably 0.05-0.5% by weight.

Thereby, the weight information in the preceding sections respectively refers to the total mass of the pertaining components.

As a rule, the proportion of ingredient g) in component A is 0-80% by weight, relative to the total mass of component A, preferably 10-70% by weight and particularly preferred 20 to 60% by weight; as a rule, the proportion of ingredient g) in component B is 10-90% by weight, relative to the total mass of component B, preferably 15-70% by weight and particularly preferred, 20 to 60% by weight.

As a rule, ingredient i) in components A and/or B is 0-20% by weight relative to the total mass of the respective component, preferably 0-15% by weight and particularly preferred, 0-10% by weight.

Preferred are polymerizable dental materials in which component A contains
  to 85% by weight of at least one reactive paste-forming agent containing component a) and/or b), and
  0.5 to 20% by weight of component c),
whereby the percentages relate to the total mass of component A, and in which component B contains
  20 to 85% by weight of component d),
  1 to 100 ppm of component e) and
  0.01 to 1% by weight of component f),
whereby the percentages relate to the total mass of component B.

A selection of the paste-forming agents according to the invention is illustrated in the exemplary embodiments.

It is an advantage of the alkenyl-group-containing compounds a) and b) that they are not polymerized by the CH-acidic barbituric acid derivatives or malonyl sulfamides during storage, as this is the case for (meth)acrylates and vinyl ethers (compare, for example, DE 100 17 188 B4); on the other hand, however, they copolymerize after the ingredients according to the invention are mixed with the (meth)acrylic acid esters, and thus form hardened products with better mechanical properties.

The initiator system based on barbituric acid derivatives and/or malonyl sulfamides can be complemented with additional initiator systems, which initiate the radical polymerization of monomers d). These can be, for example, additional initiators or initiator components different from components c), e), f), and h) such as, for example, inorganic peroxides, hydroperoxides, peracids or redox initiators, or redox initiator components and/or photo initiators. As the result of the combination of chemical and photochemical initiation, dual-hardening dental masses can be produced according to the invention.

Particularly suitable as inorganic peroxide are alkali or earth alkali peroxodisulfates, in particular, sodium or potassium peroxodisulfate. Particularly suitable as redox initiator component are alkali or earth-alkali toluolsulfinate, in particular, sodium or potassium toluolsulfinate. These additional initiators can be used particularly for acidic formulations, which can be used, for example, as self-etching cements. In such cases, the sodium peroxodisulfate in component A and the sodium toluolsulfinate can be advantageously formulated, perhaps with basic additives, in component B.

Suitable photo initiators are, for example, $\alpha$-diketones such as campherchinone in combination with secondary and tertiary amines or mono and bisacylphosphine oxides, such as 2,4,6-trimethylbenzoyl diphenylphosphine oxide and bis-(2,6-dichlorbenzoyl)-4-n-propylphenyl phosphineoxide. Other compounds of this type are also suitable as described in EP 0 073 413 A2, EP 0 007 508 A2, EP 047 902 A2, EP 057 474 A2 and EP 0 184 095 A2.

It was surprisingly found that the reactive paste-forming agents a) and/or b) containing selected alkenyl groups can be formulated with barbituric acid derivatives and/or malonyl sulfamides as initiator component A, without triggering a premature polymerization of the alkenyl groups, as would have been expected based on the prior art cited at the beginning.

It is proposed according to the invention, that component A and component B are respectively present as a paste and are spatially separate.

The use of spatially separate pastes, i.e. of initiator paste (component A) and of base paste (component B) prevents the premature formation of radicals during storage and thus the premature start of the polymerization of the two components. Moreover, pastes are an advantage for handling the polymerizable dental material, as these can be mixed manually, as well as by self-mixing systems (e.g. double cartridge with static and dynamic mixing cannulas) in a more careful way than is the case, for example, for a multi-component system that is based on powder and liquid.

Component A of the polymerizable dental material according to the present invention is stable for storage at room temperature, as well as at stress temperatures of 40° C. and sometimes also 60° C., i.e. the reactive paste-forming agents a) and/or b) containing the reactive alkenyl groups (monomers, oligomers, polymers) can form the initiator paste with barbituric acid derivatives and/or malonyl sulfamides without triggering a premature polymerization of the alkenyl groups under storage conditions. An equally good storage stability is also present in component B of the polymerizable dental material.

The multicomponent composition according to the invention is processed by mixing the individual components of the previously described dental material into a polymerizable dental mass. Preferably, a base component B is mixed with a catalyst component A in proportions of 1:2 to 20:1, particularly preferred of 1:1 to 10:1 and most particularly preferred of 10:1, 5:1, 4:1, 2:1 and 1:1. These mixtures are marked by a quick polymerization at mouth conditions.

After mixing the initiator paste A with component B (base paste), the reactive paste-forming agents containing alkenyl groups radically copolymerize with the acrylate and/or (meth)acrylate monomers or oligo polymers contained in the base paste at conditions that correspond to the temperature in the mouth of a patient (temperature ~35° C., rel. humidity ~100%). In the process, the alkenyl group-containing paste-forming agents are integrated into the network that is being created; this leads to improved mechanical properties of the hardened polymerizate.

The multicomponent system according to the invention is preferably stored in suitable primary packaging such as tubes, cans, and particularly preferred in cartridges and tubular bags as they are described, for example, in EP-A-723,807, EP-A-541,972, WO 98/44860 A1 EP-A-492,412, EP-A-492,413 and EP-A-956,908, and segmented in portions for later use.

A specific embodiment relates to the use of the polymerizable dental material described above as fastening material, bonding material, filling material, stump-build-up material, dental material for the production of inlays, onlays, of lining cups and artificial teeth, as model material, fissure sealing material, root canal sealing material, dental cement, and as temporary and permanent crown and bridge material. Most particularly preferred, the dental material according to the invention is used for the production of crowns and bridge material, whereby this means temporary and permanent provisional and definitive tooth replacement. Most particularly preferred, the dental material according to the invention is used as dental cement, in particular as self-etching dental cement.

The invention also relates to a hardened dental material that is available by mixing components A and B described above, preferably in a proportion of 1:20 to 1:1, and by polymerization of the thereby obtained polymerizable dental material.

Refinements, advantages and possibilities of uses of the invention also result from the following description of preferred exemplary embodiments. Thereby, all features described, by themselves or in any reasonable combination, form the subject-matter of the invention, even independent of their summary in the individual claims and/or their reference.

The percentages stated in the documents at hand are defined as percentages by weight (% by weight), unless otherwise specified.

The polymerized dental material for the applications cited above requires more strength than the hardened dental products according to the invention, for example, because of the biting power on the occlusion, must be very break-resistant and also be able to sufficiently stabilize the relation with the tooth stumps. By including all ingredients into the polymerized dental material, significantly better mechanical properties are achieved, as is clearly shown in the following Table 18.

EXAMPLES

In the following, the structures of the compounds 1a, 2a, 2b, 3a, 4a used in the formulations according to the invention are shown, as well as the structures of the compounds 1b, 2c, 2d, 2e, 3b, 4b that do not use formulations according to the invention (=comparative examples).

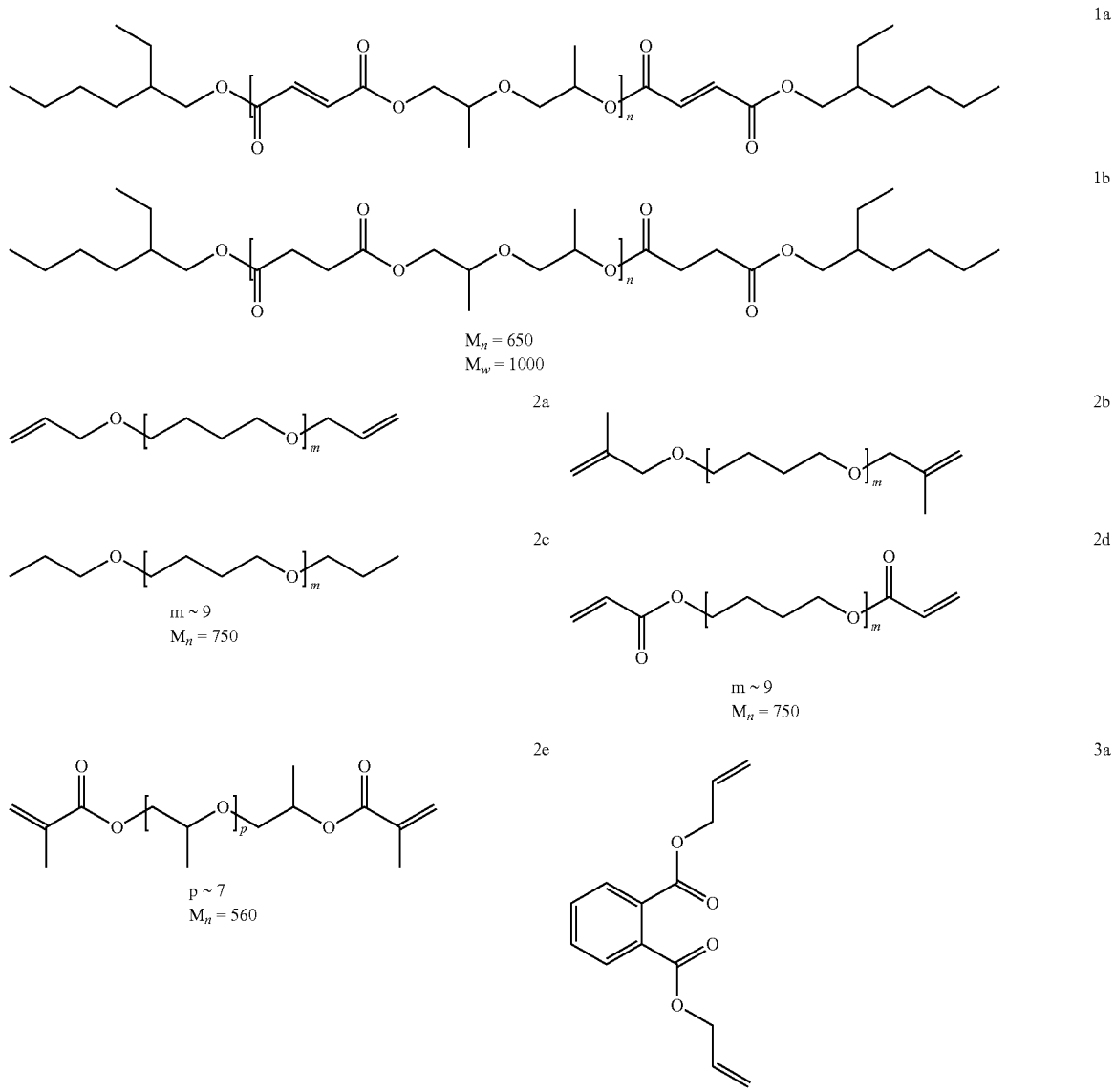

-continued

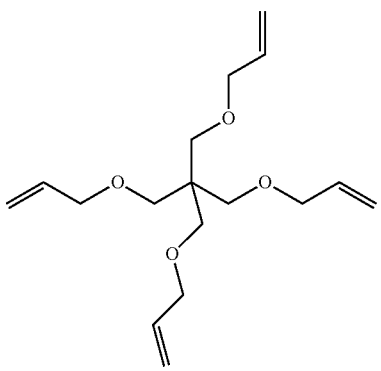

3b

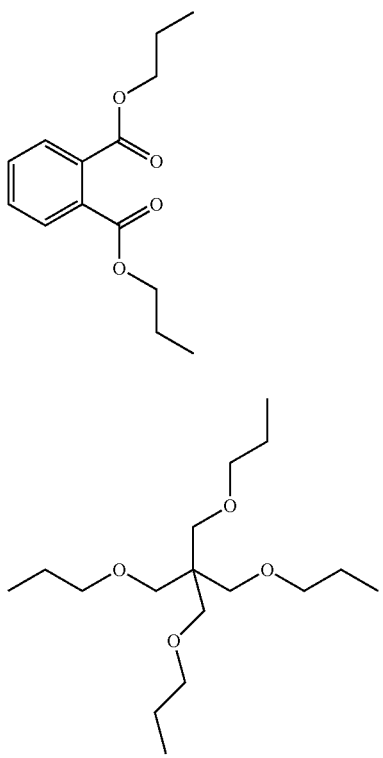

4a

4b

Production of the Starting Materials
Hydrogenation of 1a, 2a, and 4a:

100 ml of the substance to be hydrated was dissolved in 100 ml diethyl ether (abs.) and transferred to a 350 ml steel autoclave. After adding approx. 5 g Pd/C-catalyst (10% Pd), it was hydrated at a water pressure of 5 bar at 60° C. To control the progression of the reaction, the autoclave was separated from the water supply and was watched to see if additional hydrogen was being absorbed (when the pressure dropped, the hydration was continued). After 24 hours, no additional hydrogen was being absorbed. After filtering off the Pd/C catalyst, the product was concentrated and analyzed by NMR spectroscopy. All NMR spectra were taken at room temperature with a Bruker DRX-250 spectrometer ($^1$H-NMR bei 250 MHz, $^{13}$C-NMR at 62 MHz). Chemical displacements in ppm relate to the respective solvent signal ($^1$H-NMR, $^{13}$C-NMR).

Compound 1b:
$^1$H NMR (CDCl$_3$, 250 MHz): δ 4.91-5.16 (m, CH(CH$_3$)OC(O)), 3.82-4.12 (m, OCH$_2$—CH(Et)+OCH$_2$CH(CH$_3$)O), 3.58-3.82 (m, OCH$_2$CH(Me)O), 3.33-3.58 (m, OCHH$_2$CH(Me)OC(O)), 2.40-2.73 (m, C(O)CH$_2$CH$_2$C(O)), 1.42-1.62 (m, CH(Et)), 1.01-1.40 (m, CH(CHH$_3$))+CH(CH$_2$CH$_3$)CH$_2$CH$_2$CH$_2$Me), 0.73-0.96 (m, CHH$_3$CH$_2$CH$_2$).

$^{13}$C NMR (CDCl$_3$, 62 MHz): δ 172.74 (OHCH(Me)OC(O)), 172.72 (CH(Et)CH$_2$OC(O)), 172.06 (CH$_2$CH$_2$C(O)OCH$_2$), 73.84 (CH$_2$CH(Me)O), 71.93 (OCH$_2$CH(Me)OC(O)), 69.94 (OCH$_2$CH(Me)O), 67.78 (C(O)OCH$_2$CH(Me)O), 67.47 (CH(Et)CH$_2$O), 30.69 (CH(Et) CH$_2$CH$_3$), 29.71 (CH(Me)OC(O)CH$_2$CH$_2$), 29.58 (CH(Et)CH$_2$OC(O) CH$_2$), 29.44 (CH(Et)CH$_2$OC(O)CH$_2$CH$_2$), 29.40 (CH(Me)OC(O)CH$_2$CH$_2$), 29.24 (MeCH$_2$CH$_2$CH$_2$), 24.07 (CH(CH$_2$CH$_3$), 23.28 (MeCH$_2$CH$_2$CH$_2$), 17.27 (MeCHOCH$_2$), 16.88 (MeCHOC(O)), 14.35 (MeCH$_2$CH$_2$CH$_2$), 11.29 (MeCH$_2$CH).

Compound 2c:
$^1$H NMR (CDCl$_3$, 250 MHz): δ 3.18-3.37 (m, OCH$_2$), 1.39-1.57 (m, C—CH$_2$), 0.78 (t, J=7.41, CH$_3$).

$^{13}$C NMR (CDCl$_3$, 62 MHz): δ 72.85 (OCH$_2$CH$_2$CH$_3$), 70.91 (br, OCH$_2$CH$_2$CH$_2$CH$_2$O), 26.85 (OCH$_2$CH$_2$CH$_2$CH$_2$O), 23.27 (OCH$_2$CH$_2$CH$_3$), 10.93 (Me).

Compound 4b:
$^1$H NMR (DMSO, 250 MHz): δ 3.22-3.31 (t, OCHHCH$_2$), 1.38-1.56 (m, CH$_2$—CH$_2$—CH$_3$), 0.78-0.89 (t, CH$_3$).

$^{13}$C NMR (DMSO, 62 MHz): δ 72.61 (OCH$_2$CH$_2$CH$_3$), 69.45 (CCH$_2$), 45.65 (C), 22.72 (CH$_2$CH$_3$), 10.77 (CH$_3$).

To produce the initiator pastes according to the invention, the ingredients listed in the following Tables 1, 3, 4, 8, 10, 12, 14 and 15 were homogenized and dispersed using a three-roll mill. Subsequently, the initiator pastes were filled into the small chamber of a 10:1 cartridge of the Mixpac CS 050-10-06 (Sulzer) type, the large chamber was filled with the base paste that was produced in the same way according to Table 17. The masses were degassed by centrifuging, the cartridges were closed and the dental masses were discharged using a static mixer of the Mixpac MBX 3.2-16-S (Sulzer) type. For comparison, the ingredients listed in Tables 2, 5, 6, 7, 9, 11, 13 and 16 pertaining to initiator pastes not according to the invention, were processed in the same way.

The E-module and the bending strength were determined according to EN ISO 4049 (at least 8 specimens per measurement). The results are shown in Table 18.

TABLE 1

Production example of initiator paste Ia (according to the invention):

| Ingredient | Amount [%] | Amount [g] |
|---|---|---|
| Unsaturated polyester resin 1a | 47.00 | 9.40 |
| Barium glass powder, non-silanized 1.5 μm | 41.50 | 8.30 |

TABLE 1-continued

Production example of initiator paste Ia (according to the invention):

| Ingredient | Amount [%] | Amount [g] |
|---|---|---|
| 1-benzyl-5-phenylbarbituric acid | 8.00 | 1.60 |
| HDK ® H2000[1] | 3.50 | 0.70 |

TABLE 2

Production example of initiator paste Ib (comparative example, not according to the invention)

| Ingredient | Amount [%] | Amount [g] |
|---|---|---|
| Saturated polyester resin 1b | 47.00 | 9.40 |
| Barium glass powder, non-silanized 1.5 μm | 41.50 | 8.30 |
| 1-benzyl-5-phenylbarbituric acid | 8.00 | 1.60 |
| HDK ® H2000[1] | 3.50 | 0.70 |

TABLE 3

Production example of initiator paste IIa (according to the invention)

| Ingredient | Amount [%] | Amount [g] |
|---|---|---|
| Poly-THF diallylether 2a | 40.00 | 8.00 |
| Barium glass powder, non-silanized 1.5 μm | 48.50 | 9.70 |
| 1-benzyl-5-phenylbarbituric acid | 8.00 | 1.60 |
| HDK ® H2000[1] | 3.50 | 0.70 |

TABLE 4

Production example of initiator paste IIb (according to the invention)

| Ingredient | Amount [%] | Amount [g] |
|---|---|---|
| Poly-THF-dimethallyl ether 2b | 40.00 | 8.00 |
| Barium glass powder, non-silanized 1.5 μm | 48.50 | 9.70 |
| 1-benzyl-5-phenylbarbituric acid | 8.00 | 1.60 |
| HDK ® H2000[1] | 3.50 | 0.70 |

TABLE 5

Production example of initiator paste IIc (comparative example, not according to the invention)

| Ingredient | Amount [%] | Amount [g] |
|---|---|---|
| Poly-THF-dipropyl ether 2c | 40.00 | 8.00 |
| Barium glass powder, non-silanized 1.5 μm | 48.50 | 9.70 |
| 1-benzyl-5-phenylbarbituric acid | 8.00 | 1.60 |
| HDK ® H2000[1] | 3.50 | 0.70 |

TABLE 6

Production example of initiator paste IId (comparative example, not according to the invention)

| Ingredient | Amount [%] | Amount [g] |
|---|---|---|
| Poly-THF diacrylate 2d | 40.00 | 8.00 |
| Barium glass powder, non-silanized 1.5 μm | 48.50 | 9.70 |
| 1-benzyl-5-phenylbarbituric acid | 8.00 | 1.60 |
| HDK ® H2000[1] | 3.50 | 0.70 |

TABLE 7

Production example of initiator paste IIe (comparative example, not according to the invention)

| Ingredient | Amount [%] | Amount [g] |
|---|---|---|
| Poly(propyleneglycol)-dimethacrylate 2e | 40.00 | 8.00 |
| Barium glass powder, non-silanized 1.5 μm | 48.50 | 9.70 |
| 1-benzyl-5-phenylbarbituric acid | 8.00 | 1.60 |
| HDK ® H2000[1] | 3.50 | 0.70 |

TABLE 8

Production example of initiator paste IIIa (according to the invention)

| Ingredient | Amount [%] | Amount [g] |
|---|---|---|
| Diallyl phthalate 3a | 41.00 | 8.20 |
| Barium glass powder, non-silanized 1.5 μm | 47.50 | 9.50 |
| 1-benzyl-5-phenylbarbituric acid | 8.00 | 1.60 |
| HDK ® H2000[1] | 3.50 | 0.70 |

TABLE 9

Production example of initiator paste IIIb (comparative example, not according to the invention)

| Ingredient | Amount [% by weight] | Amount [g] |
|---|---|---|
| Dipropyl phthalate 3b | 41.00 | 8.20 |
| Barium glass powder, non-silanized 1.5 μm | 47.50 | 9.50 |
| 1-Benzyl-5-phenylbarbituric acid | 8.00 | 1.60 |
| HDK ® H2000[1] | 3.50 | 0.70 |

TABLE 10

Production example of initiator paste IVa (according to the invention)

| Ingredient | Amount [%] | Amount [g] |
|---|---|---|
| Tetraallyl pentaerytriol 4a | 41.00 | 8.,20 |
| Barium glass powder, non-silanized 1.5 μm | 47.50 | 9.50 |
| 1-benzyl-5-phenylbarbituric acid | 8.00 | 1.60 |
| HDK ® H2000[1] | 3.50 | 0.70 |

TABLE 11

Production example of initiator paste IVb (comparative example, not according to the invention)

| Ingredient | Amount [%] | Amount [g] |
|---|---|---|
| Tetrapropyl pentaerytriol 4b | 41.00 | 8.20 |
| Barium glass powder, non-silanized 1.5 μm | 47.50 | 9.50 |
| 1-benzyl-5-phenylbarbituric acid | 8.00 | 1.60 |
| HDK ® H2000[1] | 3.50 | 0.70 |

TABLE 12

Production example of initiator paste Va with perester (according to the invention)

| Ingredient | Amount [%] | Amount [g] |
|---|---|---|
| Unsaturated polyester resin 1a | 46.00 | 4.60 |
| Barium glass powder, non-silanized 1.5 μm | 41.50 | 4.15 |
| 1-benzyl-5-phenylbarbituric acid | 8.00 | 0.80 |
| HDK H2000[1] | 3.50 | 0.35 |
| tert.-butylperoxy-3,5,5-trimethylhexanoat | 1.00 | 0.10 |

TABLE 13

Production example of initiator paste Vb with perester (comparative example, not according to the invention)

| Ingredient | Amount [%] | Amount [g] |
|---|---|---|
| Saturated polyester resin 1b | 46.00 | 4.60 |
| Barium glass powder, non-silanized 1.5 μm | 41.50 | 4.15 |
| 1-Benzyl-5-phenylbarbituric acid | 8.00 | 0.80 |
| HDK ® H2000[1] | 3.50 | 0.35 |
| tert.-butylperoxy-3,5,5-trimethylhexanoat | 1.00 | 0.10 |

TABLE 14

Production example of initiator paste VIa with perester (according to the invention)

| Ingredient | Amount [%] | Amount [g] |
|---|---|---|
| Poly-THF diallylether 2a | 39.00 | 3.90 |
| Barium glass powder, non-silanized 1.5 μm | 48.50 | 4.85 |
| 1-benzyl-5-phenylbarbituric acid | 8.00 | 0.80 |
| HDK ® H2000[1] | 3.50 | 0.35 |
| tert.-butylperoxy-3,5,5-trimethylhexanoat | 1.00 | 0.10 |

TABLE 15

Production example of initiator paste VIb with perester (according to the invention)

| Ingredient | Amount [%] | Amount [g] |
|---|---|---|
| Poly-THF-dimethallylether 2b | 39.00 | 3.90 |
| Barium glass powder, non-silanized 1.5 μm | 48.50 | 4.85 |
| 1-benzyl-5-phenylbarbituric acid | 8.00 | 0.80 |
| HDK ® H2000[1] | 3.50 | 0.35 |
| tert.-butylperoxy-3,5,5-trimethylhexanoat | 1.00 | 0.10 |

TABLE 16

Production example of initiator paste VIc with perester (comparative example, not according to the invention)

| Ingredient | Amount [%] | Amount [g] |
|---|---|---|
| Poly-THF dipropylether 2c | 39.00 | 3.90 |
| Barium glass powder, non-silanized 1.5 μm | 48.50 | 4.85 |
| 1-Benzyl-5-phenylbarbituric acid | 8.00 | 0.80 |
| HDK ® H2000[1] | 3.50 | 0.35 |
| tert.-butylperoxy-3,5,5-trimethylhexanoate | 1.00 | 0.10 |

TABLE 17

Production example of base paste VII

| Ingredient | Amount [%] | Amount [g] |
|---|---|---|
| ethoxylated bisphenol-A-di(meth)acrylate (4EO) | 42.50 | 85.00 |
| aliphatic urethanedi(meth)acrylate | 13.50 | 27.00 |
| Barium glass powder 1.5 μm, (meth)acrylate silanized | 36.58 | 73.16 |
| Aerosil DT4[2] | 7.00 | 14.00 |
| 4-Hydroxyanisol | 0.10 | 0.20 |
| Copper(II)di(meth)acrylate in hydroxyethyl(meth)acrylate (1% sln.) | 0.12 | 0.24 |
| Dodecyltrimethylammonium chloride | 0.20 | 0.40 |

[1] The ingredient HDK ® H2000 is a pyrogenic silicic acid that is surface-modified with trimethylsiloxy groups having a carbon content of 2.5% and a specific BET surface of 140 $m^2/g$ (according to DIN 66131 and DIN 66132), which can be obtained under this name from Wacker-Chemie GmbH, Munich, Germany.
[2] The ingredient Aerosil DT4 is a methacrylate silanized hydrophobic silicium oxide, which can be obtained under this name at Evonik Degussa GmbH, Frankfurt/Main, Germany.

TABLE 18

Results of hardened products from mixtures consisting of base paste according to Table 17 and various initiator pastes

| Initiator Paste No. | E-Module[1] [MPa] | Bending Strength[1] [MPa] |
|---|---|---|
| Ia | 3391 ± 87 | 104 ± 4 |
| Ib | 3107 ± 147 | 94 ± 5 |
| IIa | 3775 ± 158 | 109 ± 7 |
| IIb | 3411 ± 143 | 100 ± 1 |
| IIc | 2901 ± 117 | 84 ± 3 |
| IId | [2] | [2] |
| IIe | [2] | [2] |
| IIIa | 4034 ± 184 | 111 ± 6 |
| IIIb | 3268 ± 143 | 95 ± 4 |
| IVa | 4023 ± 100 | 109 ± 5 |
| IVb | 2981 ± 135 | 88 ± 4 |
| Va | 4963 ± 70 | 139 ± 3 |
| Vb | 4627 ± 107 | 130 ± 6 |
| VIa | 4736 ± 168 | 134 ± 6 |
| VIb | 5160 ± 265 | 145 ± 3 |
| VIc | 4381 ± 158 | 120 ± 7 |

[1] Deviation in σ (standard deviation)
[2] The initiator paste hardened prematurely as separate component and was therefore not stable for storage.

It can be seen in Table 18 that compared to the known dental material containing non-reactive paste-forming agents (i.e. without alkenyl groups), as they are described in prior art, the polymerizable dental materials containing reactive paste-forming agents according to the present invention achieve significantly better mechanical properties in the final product subsequent to polymerization. This is documented, for example, by higher bending strengths and E-moduli in the three-point-bending test.

To examine the storage stability, the cartridges Ia, Ib, IIa, IIb, IIc, IId, IIe, IIIa, IIIb, IVa and IVb were stored at 60° C., 37° C., and at room temperature. While the contents of all cartridges Ia, Ib, IIa, IIb, IIc, IIIa, IIIb, IVa and IVb were paste-like after having been stored for four weeks, and hardened within the expected time after being discharged via a static mixer, in cartridge IId and IIe, premature hardening of the material was observed. The content of the cartridge stored at 60° C. was hardened after three hours already (IId) or after one hour (IIe), the cartridge stored at 37° C. after 24 hours (IId) or after five hours (IIe) and the cartridge stored at room temperature after two days (IId) or after 22 hours (IIe).

Cartridges Va, Vb, VIa, VIb and VIc containing peresters as ingredients were stored at 37° C. and at room temperature. In all cases, the contents were paste-like after having been stored for four weeks, and hardened within the expected time after being discharged by a static mixer. The formulations according to the invention exhibited significantly better mechanical properties.

What is claimed is:

1. A polymerizable dental material system comprising
at least one paste-like component A and
at least one paste-like component B substantially separate from component A,
wherein component A comprises
at least one initiator of radical polymerization c) selected from the group consisting of barbituric acid derivatives and malonyl sulfamides; and
and a reactive paste-forming agent comprising at least one organic compound a) derived from maleic acid and/or fumaric acid and/or itaconic acid that has no additional ethylenically unsaturated groups in addition to the groups derived from maleic acid and/or fumaric acid and/or itaconic acid, and/or at least one compound b) comprising at least one allyl and/or methallyl residue and if appropriate, units derived from maleic acid and/or fumaric acid and/or itaconic acid that do not contain any ethylenically unsaturated groups in addition to the ethylenically unsaturated groups cited above; and wherein component B comprises an organic compound d) comprising at least one acrylic acid ester and/or methacrylic acid ester residues, at least one metal compound e) and at least one halide or pseudo halide compound f).

2. A polymerizable dental material system as recited in claim 1, wherein the reactive paste-forming agent of Component A contains at least one organic compound a) derived from maleic acid and/or fumaric acid that has no ethylenically unsaturated groups other than those groups derived from maleic acid and/or fumaric acid, and/or at least one compound b) comprising at least one allyl and/or methallyl residue and, if appropriate, units derived from maleic acid and/or fumaric acid that do not contain any ethylenically unsaturated groups in addition to the ethylenically unsaturated groups cited above.

3. A polymerizable dental material system as recited in claim 1, wherein ingredient a) contains at least one organic compound represented by the Formulas Ia, Ib, IIa, IIb, IIc or IId:

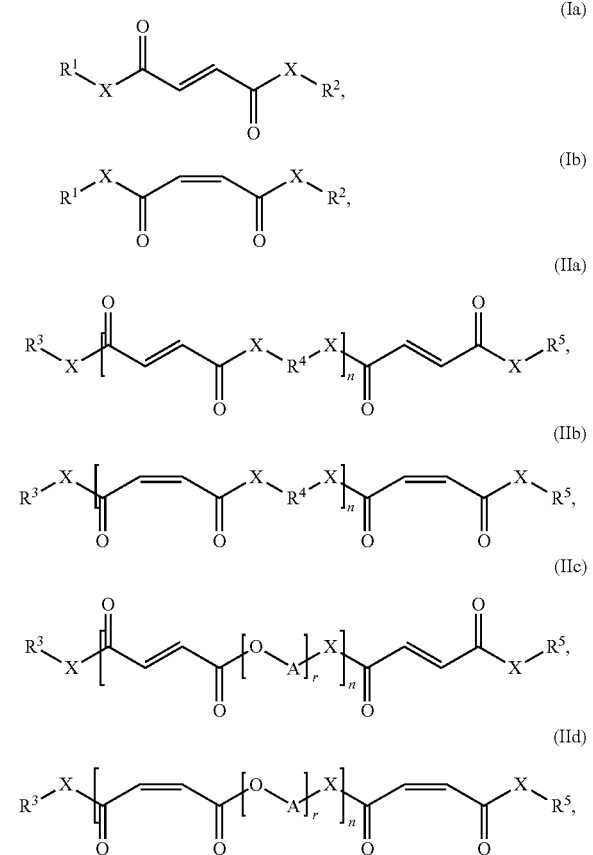

in which
X is oxygen or $-NR^6-$ is a group,
$R^1$, $R^2$, $R^3$ and $R^5$, independent of each other, mean alkyl, cycloalkyl, alkyl cycloalkyl, aryl, alkyl aryl, aralkyl or heterocyclyl, which have, if appropriate, one or more substituents, $R^4$ means alkylene, alkylene glycol ether, cycloalkylene, alkyl cycloalkylene, arylene, alkyl arylene, aralkylene or heterocyclylene that has, if appropriate, one or more substituents, $A=CH_2-CH_2$, $CH_2-CH(CH_3)$ or $CH_2-CH_2-CH_2$, $R^6$ is hydrogen, alkyl, cycloalkyl, alkyl cycloalkyl, aryl, alkyl aryl, aralkyl or heterocyclyl, n is a whole number from 1 to 50, and r is a whole number from 1 to 100.

4. A polymerizable dental material system as recited in claim 3, wherein ingredient a) comprises a compound of any of Formulas Ia, Ib, IIa, IIb, IIc and IId having one or more residues $R^1$ to $R^5$ having a substituent with acidic function, or ingredient a) comprises a compound of any of Formulas Ia, Ib, IIa, IIb, IIc and IId having one or more of the residues $R^1$ to $R^5$ having a substituent with acidic function and hydroxyl groups as substituents, or ingredient a) comprises a mixture of a compound of any of Formulas Ia, Ib, IIa, IIb, IIc and IId having one or more residues $R^1$ to $R^5$ having a hydroxyl group as a substituent and a compound of any of Formulas Ia, Ib, IIa, IIb, IIc and IId having one or more residues $R^1$ to $R^5$ having a substituent with acidic function.

5. A polymerizable dental material system as recited in claim 1, wherein ingredient b) comprises a compound represented by Formula III

in which
$R^7$ is an m-valent residue that optionally has one or several substituents,
$R^8$ is a $-CH_2-CR^9=CH_2$ group,
$R^9$ means hydrogen or methyl,
m is a whole number from 1 to 12, and
Y is selected from the group of covalent bonds and a bivalent residue.

6. A polymerizable dental material system as recited in claim 5, wherein ingredient b) comprises a compound of Formula (III) in which the residue $R^7$ has a substituent with acidic function, or ingredient b) comprises a compound of Formula (III) in which the residue, $R^7$ has a substituent with acidic function and a hydroxyl group as substituents, or ingredient b) comprises a mixture of compounds of Formula (III), the mixture including a compound in which the residue $R^7$ has a substituent with acidic function and a compound in which the residue $R^7$ has a hydroxyl group as a substituent.

7. A polymerizable dental material system as recited in claim 1, wherein ingredient c) is selected from the group of compounds represented by Formula IV, V or VI

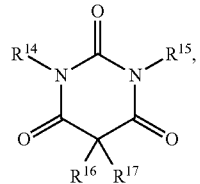

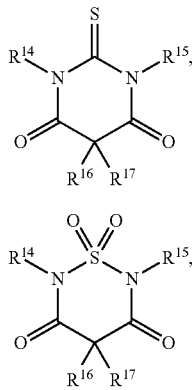

in which
R$^{16}$ and R$^{17}$, independent of each, other mean hydrogen, alkyl, alkenyl, cycloalkyl, aryl, aralkyl and heterocyclyl, provided that at least one of the residues R$^{16}$ or R$^{17}$ means hydrogen, and
R$^{14}$ and R$^{15}$, independent of each, other mean hydrogen, alkyl, alkenyl, cycloalkyl, aryl, aralkyl and heterocyclyl, in particular, from the group of barbituric acid derivatives represented by Formula IV,
in which R$^{14}$ and/or R$^{16}$ or R$^{17}$, independent of each other, mean alkyl, cycloalkyl, aryl or aralkyl.

8. A polymerizable dental material system as recited in claim 1, wherein ingredient d) is an organic compound represented by the Formula VII:

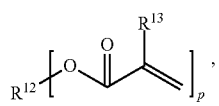

in which
R$^{12}$ is a p-valent organic residue, that optionally has one or more substituents,
R$^{13}$ means hydrogen or methyl, and
p is a whole number from 1 to 12.

9. A polymerizable dental material system as recited in claim 1, wherein ingredient e) is a metal compound that is selected from the group of metal salts and/or metal complexes.

10. A polymerizable dental material system as recited in claim 1, wherein ingredient f) is a salt soluble at 25° C. in ingredient d).

11. A polymerizable dental material system as recited in claim 1, wherein component A and/or B additionally contains at least one filler g).

12. A polymerizable dental material system as recited in claim 1, wherein component A and/or component B additionally contains at least one organic peroxide h).

13. A polymerizable dental material system as recited in claim 1, wherein component A contains
   10 to 85% by weight of at least one reactive paste-forming agent of component a) and/or b), and
   0.5 to 20% by weight of component c),
in which the percentage information relates to the total mass of component A, and
wherein component B contains
   20 to 85% by weight of component d),
   1 to 100 ppm of component e) and
   0.01 to 1% by weight of component f),
in which the percentage information relates to the total mass of component B.

14. A polymerizable dental material system as recited in claim 1, wherein the dental material in component A and/or B contains one or more additives i), selected from the group consisting of buffer salts, water scavengers, metal scavengers, metal complex-forming agents, additional paste-forming agents, tensides, active ingredients, substances making optical scanning possible, flavoring substances and/or odorants, substances making diagnostics possible, tooth substance etching and/or substances with adhesive-action, fluoridation agents, bleaching substances, desensitizing agents, composite adhesive agents, colorants, pigments, indicators, additional components c), e), and/or f), indicators or indicator components, stabilizers, polymerization inhibitors, thixotropy aids and antibacterial substances, or combinations of two or more of such.

15. A hardened dental material obtainable by a method comprising providing a polymerizable dental material system as recited in claim 1, mixing components A and B in a proportion of 1:20 to 1:1 to form a polymerizable dental material, and polymerizing the polymerizable dental material.

16. The hardened dental material as recited in claim 15, wherein the hardened dental material is configured as a fastening material, a bonding material, a filling material, a stump-build-up material, a dental material for producing inlays, onlays, cup liners or artificial teeth, a model material, a fissure sealing material, a root canal sealing material, a dental cement or a temporary or permanent crown or bridge material.

17. A method for making a polymerizable dental material, the method comprising providing a polymerizable dental material system as recited in claim 1, and mixing components A and B in a proportion of 1:20 to 1:1 to form the polymerizable dental material.

18. A method for making a hardened dental material, the method comprising providing a polymerizable dental material system as recited in claim 1, mixing components A and B in a proportion of 1:20 to 1:1 to form a polymerizable dental material, and polymerizing the polymerizable dental material.

19. A method as recited in claim 18, wherein the hardened dental material is used as a fastening material, a bonding material, a filling material, a stump-build-up material, a dental material for producing inlays, onlays, cup liners or artificial teeth, a model material, a fissure sealing material, a root canal sealing material, a dental cement or a temporary or permanent crown or bridge material.

20. A method as recited in claim 18, wherein the hardened dental material is used for the production of crowns and bridge material or as dental cement.

21. A polymerizable dental material system as recited in claim 1, wherein ingredient a) contains at least one organic compound that contains maleic acid diester and/or fumaric acid diester residues or that contains maleic acid diamides and/or fumaric acid diamides residues.

22. A polymerizable dental material system as recited in claim 1, wherein ingredient b) is a compound containing allyl ether and/or methallyl ether residues and which does not contain any other ethylenically unsaturated groups.

23. A polymerizable dental material system as recited in claim 4, wherein each acidic function is selected from the group consisting of phosphoric acid groups, phosphonic acid groups, sulfonic acid groups and carboxylic acid groups, and anhydrides thereof.

24. A polymerizable dental material system as recited in claim 6, wherein each acidic function is selected from the group consisting of phosphoric acid groups, phosphonic acid groups, sulfonic acid groups and carboxylic acid groups, and anhydrides thereof.

25. A polymerizable dental material system as recited in claim 9, wherein ingredient e) is a metal compound that is selected from the group consisting of the salts of the metals of the third and fourth main group and the first to the eighths secondary group of the periodic table of the elements and the complexes of metals of the third and fourth main group and the first to eighth secondary group of the periodic table of the elements.

26. A polymerizable dental material system as recited in claim 25, wherein the metal of the metal compound is a lanthanide.

27. A polymerizable dental material system as recited in claim 25, wherein the salts comprise anions derived from carboxylic acids, and the complexes comprise ligands derived from beta-carbonyl compounds.

28. A polymerizable dental material system as recited in claim 9, wherein ingredient e) is a salt or complex of copper, iron, tin, chromium, manganese, cobalt, zinc, nickel, a rare earth or aluminum.

29. A polymerizable dental material system as recited in claim 9, wherein ingredient e) is a salt or complex of copper.

30. A polymerizable dental material system as recited in claim 10, wherein ingredient f) is a halide or pseudo halide salt, the halide or pseudo halide salt having as its cation a cation of a metal of the first or second main group of the periodic table, an ammonium cation or a phosphonium cation.

31. A polymerizable dental material system as recited in claim 10, wherein ingredient f) is a thiocyanate, isothiocyanate, cyanate or isocyanate, that has a lithium cation or a sodium cation or an ammonium cation or a phosphonium cation as cation, or a hydro-halide of a tertiary amine.

32. A polymerizable dental material system as recited in claim 10, wherein ingredient f) is a lithium, ammonium or phosphonium halide.

33. A polymerizable dental material system as recited in claim 11, wherein at least one filler g) is present in component A in a quantity of 0 to 80% by weight of component A and/or at least one filler g) is present in component B in a quantity of 10 to 90% by weight of component B.

34. A polymerizable dental material system as recited in claim 1, wherein component A and/or component B additionally contains at least one organic peroxide h), in an amount up to 5% by weight, each organic peroxide h) being selected from the group of carboxylic acids and carbonic acid peroxyesters and perketals.

35. A polymerizable dental material system as recited in claim 34, wherein each organic peroxide is selected from the group of tert-butylperoxy-3,5,5-trimethyl hexanoate, tert-butyl peroxybenzoate, tert-butylperoxy-2-ethylhexylcarbonate or combinations of two or more of such.

36. A polymerizable dental material system as recited in claim 1, wherein
   ingredient a) is an organic compound represented by the Formulas Ia, Ib, IIa, IIb, IIc or IId:

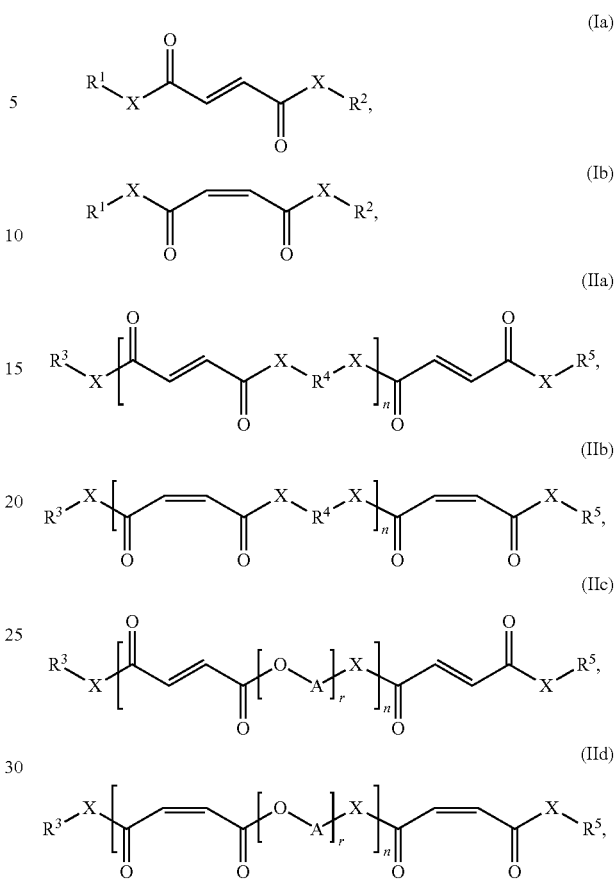

in which
   X is oxygen or —NR$^6$— is a group,
   R$^1$, R$^2$, R$^3$ and R$^5$, independent of each other, mean alkyl, cycloalkyl, alkyl cycloalkyl, aryl, alkyl aryl, aralkyl or heterocyclyl, which have, if appropriate, one or more substituents,
   R$^4$ means alkylene, alkylene glycol ether, cycloalkylene, alkyl cycloalkylene, arylene, alkyl arylene, aralkylene or heterocyclylene that has, if appropriate, one or more substituents,
   A=CH$_2$—CH$_2$, CH$_2$—CH(CH$_3$) or CH$_2$—CH$_2$—CH$_2$—CH$_2$,
   R$^6$ is hydrogen, alkyl, cycloalkyl, alkyl cycloalkyl, aryl, alkyl aryl, aralkyl or heterocyclyl,
   n is a whole number from 1 to 50, and
   r is a whole number from 1 to 100;
ingredient b) comprises a compound represented by Formula III

in which
   R$^7$ is an m-valent residue that optionally has one or several substituents,
   R$^8$ is a —CH$_2$—CR$^9$=CH$_2$ group,
   R$^9$ means hydrogen or methyl,
   m is a whole number from 1 to 12, and
   Y is selected from the group of covalent bonds and a bivalent residue;
ingredient c) is selected from the group of compounds represented by Formula IV, V or VI

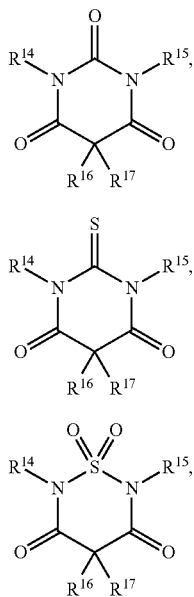

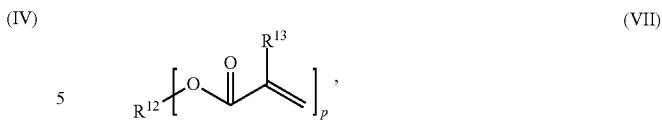

in which
R$^{16}$ and R$^{17}$, independent of each, other mean hydrogen, alkyl, alkenyl, cycloalkyl, aryl, aralkyl and heterocyclyl, provided that at least one of the residues R$^{16}$ or R$^{17}$ means hydrogen, and R$^{14}$ and R$^{15}$, independent of each, other mean hydrogen, alkyl, alkenyl, cycloalkyl, aryl, aralkyl and heterocyclyl, in particular, from the group of barbituric acid derivatives represented by Formula IV, in which R$^{14}$ and/or R$^{16}$ or R$^{17}$, independent of each other, mean alkyl, cycloalkyl, aryl or aralkyl;

ingredient d) is an organic compound represented by the Formula VII:

in which
R$^{12}$ is a p-valent organic residue, that optionally has one or more substituents, R$^{13}$ means hydrogen or methyl, and p is a whole number from 1 to 12;

ingredient e) is a metal compound that is selected from the group of the salts of the metals of the third and fourth main group and the first to the eighths secondary group of the periodic table of the elements and the complexes of metals of the third and fourth main group and the first to eighth secondary group of the periodic table of the elements; and ingredient f) is a halide or pseudo halide salt soluble at 25° C. in ingredient d), the halide or pseudo halide salt having as its metal cations of metals in the first and second main group of the periodic table, ammonium cations or phosphonium cations.

37. A polymerizable dental material system as recited in claim 36, wherein component A contains
  10 to 85% by weight of at least one reactive paste-forming agent of component a) and/or b), and
  0.5 to 20% by weight of component c),
in which the percentage information relates to the total mass of component A, and wherein component B contains
  20 to 85% by weight of component d),
  1 to 100 ppm of component e) and
  0.01 to 1% by weight of component f),
in which the percentage information relates to the total mass of component B.

* * * * *